(12) United States Patent
Thoma et al.

(10) Patent No.: US 11,208,629 B2
(45) Date of Patent: Dec. 28, 2021

(54) NON-HUMAN PRIMATE INDUCED PLURIPOTENT STEM CELL DERIVED HEPATOCYTES AND USES THEREOF

(71) Applicant: Hoffmann-La Roche Inc., Little Falls, NJ (US)

(72) Inventors: Eva Christina Thoma, Basel (CH); Martin Graf, Basel (CH); Vanessa Hunt, Basel (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 16/257,671

(22) Filed: Jan. 25, 2019

(65) Prior Publication Data

US 2019/0292518 A1 Sep. 26, 2019

Related U.S. Application Data

(63) Continuation of application No. PCT/EP2017/068668, filed on Jul. 24, 2017.

(30) Foreign Application Priority Data

Jul. 28, 2016 (EP) .................................... 16181715

(51) Int. Cl.
*C12N 5/00* (2006.01)
*C12N 5/02* (2006.01)
*C12N 5/10* (2006.01)
*C12N 5/071* (2010.01)

(52) U.S. Cl.
CPC .......... *C12N 5/067* (2013.01); *C12N 2500/24* (2013.01); *C12N 2500/25* (2013.01); *C12N 2500/62* (2013.01); *C12N 2500/92* (2013.01); *C12N 2501/115* (2013.01); *C12N 2501/119* (2013.01); *C12N 2501/12* (2013.01); *C12N 2501/155* (2013.01); *C12N 2501/16* (2013.01); *C12N 2501/237* (2013.01); *C12N 2501/39* (2013.01); *C12N 2501/415* (2013.01); *C12N 2501/727* (2013.01); *C12N 2501/999* (2013.01); *C12N 2503/02* (2013.01); *C12N 2506/45* (2013.01); *C12N 2533/54* (2013.01); *C12N 2533/90* (2013.01)

(58) Field of Classification Search
CPC ................. C12N 5/0606; C12N 5/067; C12N 2501/115; C12N 2501/12; C12N 2501/155; C12N 2506/02; C12N 2506/45
See application file for complete search history.

(56) References Cited

U.S. PATENT DOCUMENTS

2016/0256672 A1* 9/2016 Arumugaswami et al.
2018/0030415 A1* 2/2018 Nguyen et al.
2018/0258400 A1* 9/2018 Ng et al.

FOREIGN PATENT DOCUMENTS

EP 2 671 944 A1 12/2013

OTHER PUBLICATIONS

Ding et al., "A TALEN Genome-Editing System for Generating Human Stem Cell-Based Disease Models" Cell Stem Cell 12:238-251 (2013).
Ding et al., "Supplemental Information: A Transcription Activator-like Effector Nuclease Genone-Editing System for Generating Human Stem Cell-Based Disease Models" Cell Stem Cell 12 ( 2013).
Gong et al., "Discovery of potent and bioavailable GSK-3β inhibitors" Bioorganic & Medicinal Chemistry Letters 20:1693-1696 ( 2010).
Gouon-Evans et al., "BMP-4 is required for hepatic specification of mouse embryonic stem cell-derived definitive endoderm" Nature Biotechnology 24(11): 1402-1411 ( 2006).
ISR and Written Opinion for PCT/EP2017/068668 (dated Sep. 4, 2017).
Sourisseau et al., "Hepatic Cells Derived From Induced Pluripotent Stem Cells of Pigtail Macaques Support Hepatitis C Virus Infection" Gastroenterology 145(5):966-969.e7 (2013).
Sourisseau et al., "Supplementary Material" Gastroenterology 145(5):e1-e7 (2013).

* cited by examiner

Primary Examiner — Shin Lin Chen
(74) Attorney, Agent, or Firm — Jonathan P. Aumais

(57) ABSTRACT

This application relates to non-human primate (NHP) induced pluripotent stem cell (IPSC)-derived hepatocytes, for example, Cynomolgus monkey (*Macaca fascicularis*) induced pluripotent stem cell-derived hepatocytes, and methods of producing the same. Moreover, this application relates to methods of using NHP IPSC-derived hepatocytes for drug screening, drug safety assessment and in models of infection.

11 Claims, 17 Drawing Sheets

Figure 2:
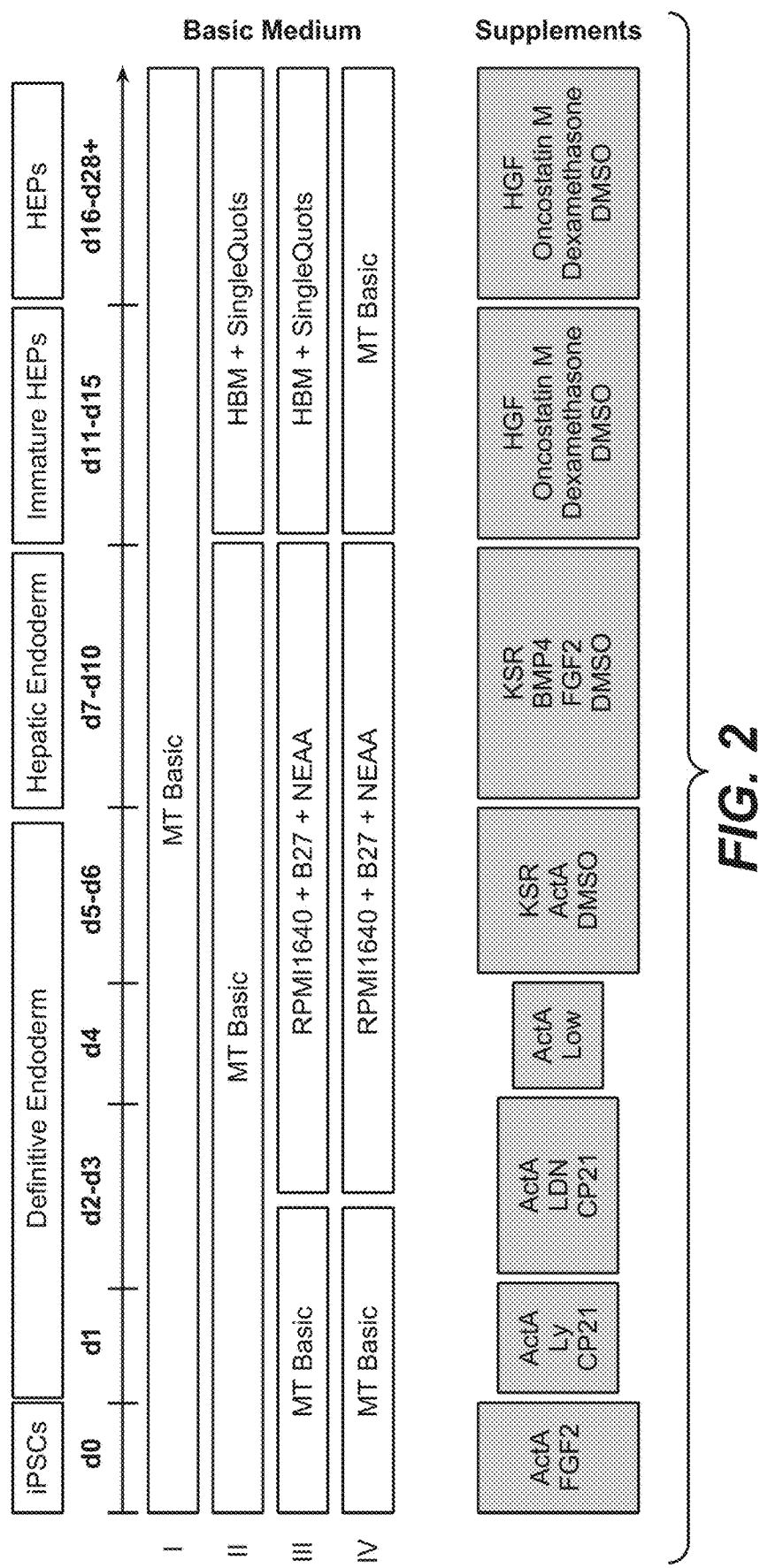

FIG. 1A
OCT4/Nuclei
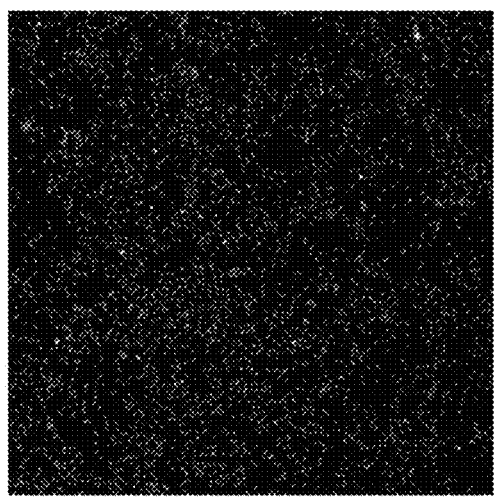
FIG. 1B
SOX2/Nuclei
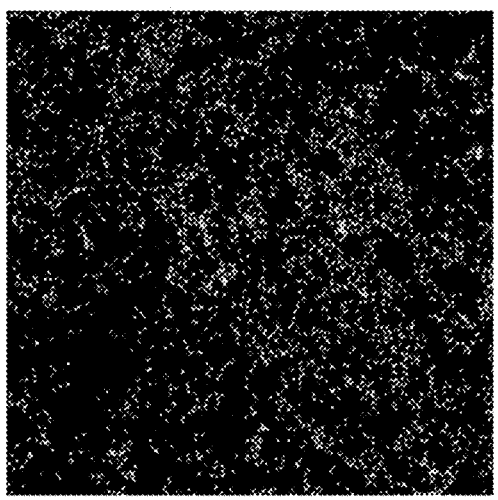
NANOG/Nuclei
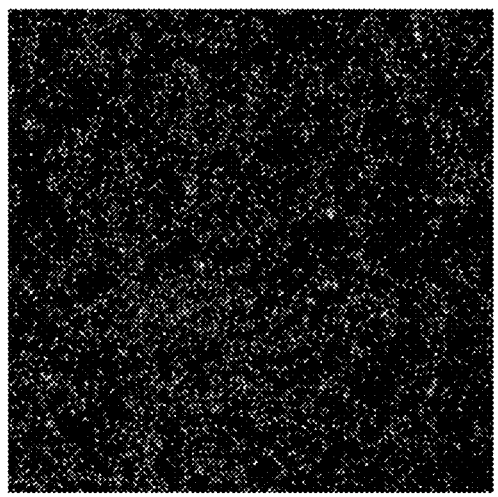
SOX1/Nuclei
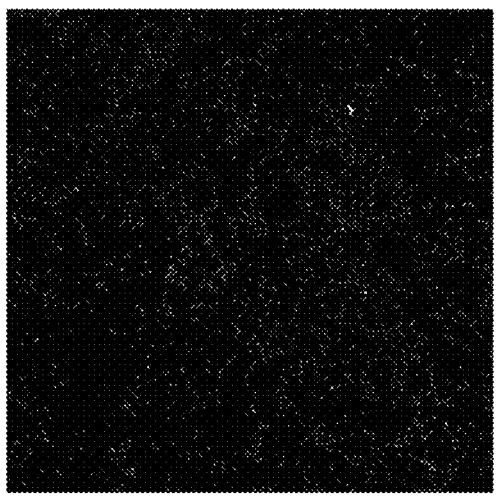
FIG. 1C
FIG. 1D
FIG. 1E
| Antigen | Positive Cells (%) |
|---------|--------------------|
| OCT4    | 93.4               |
| SOX2    | 91.4               |
| NANOG   | 95.7               |
| SOX1    | 0                  |

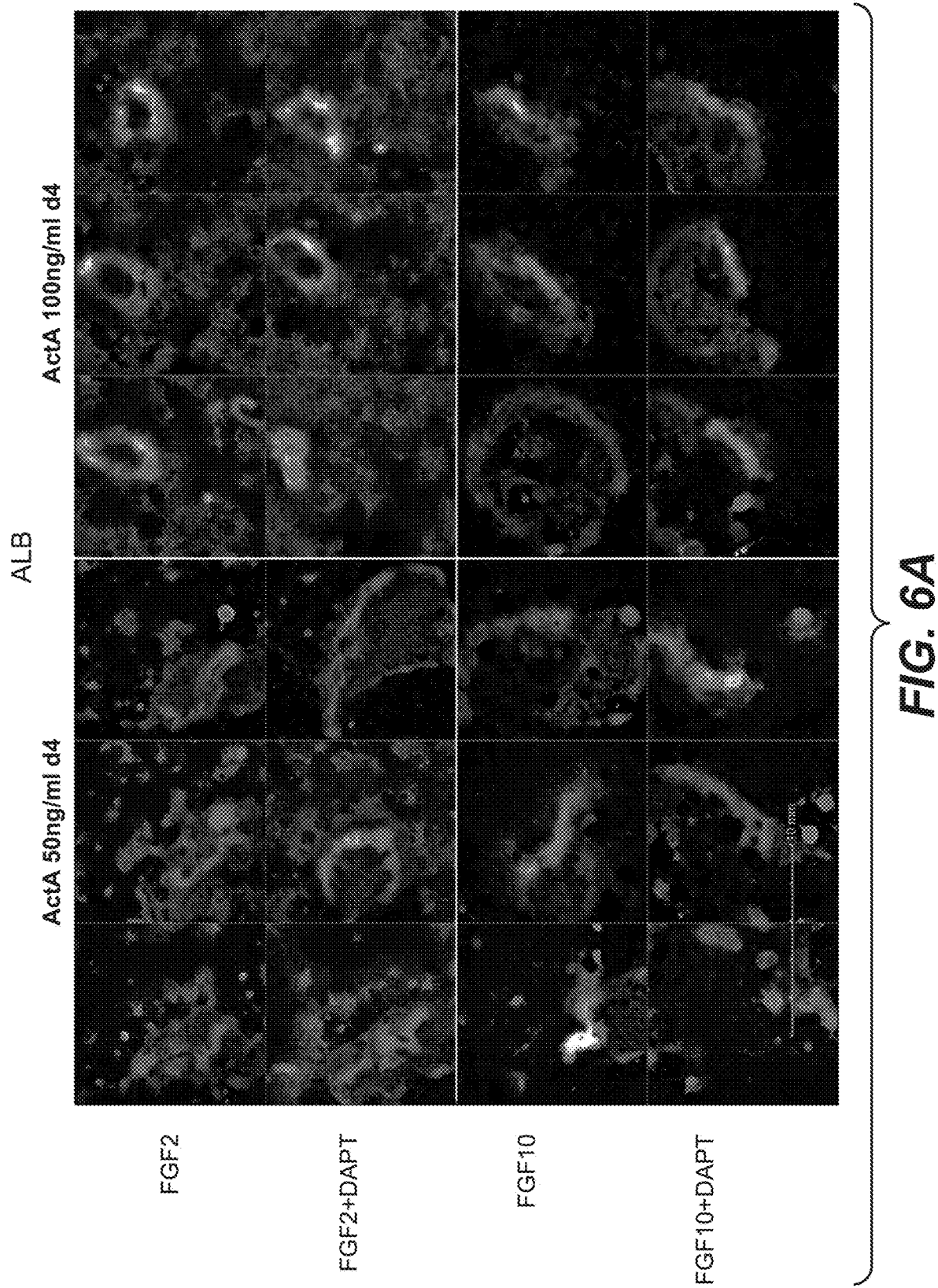

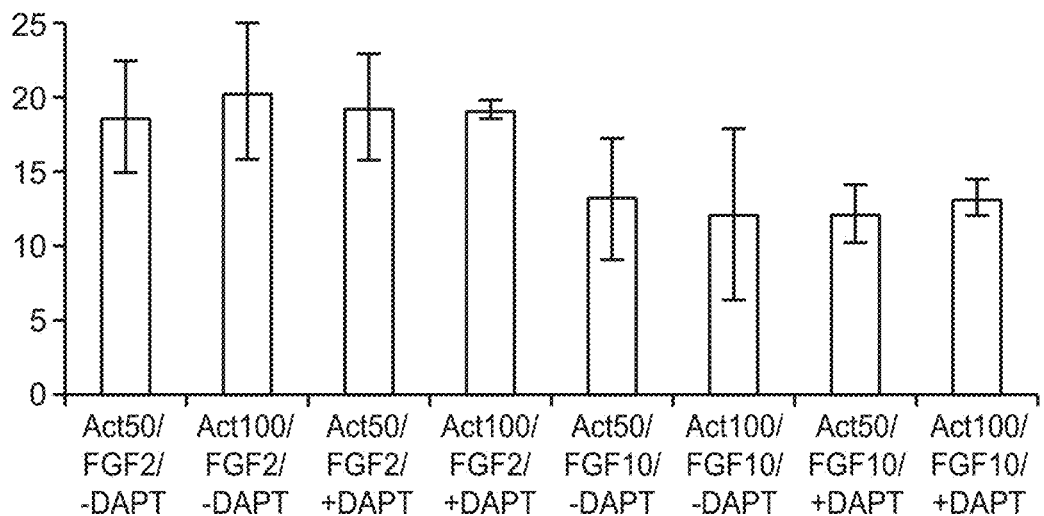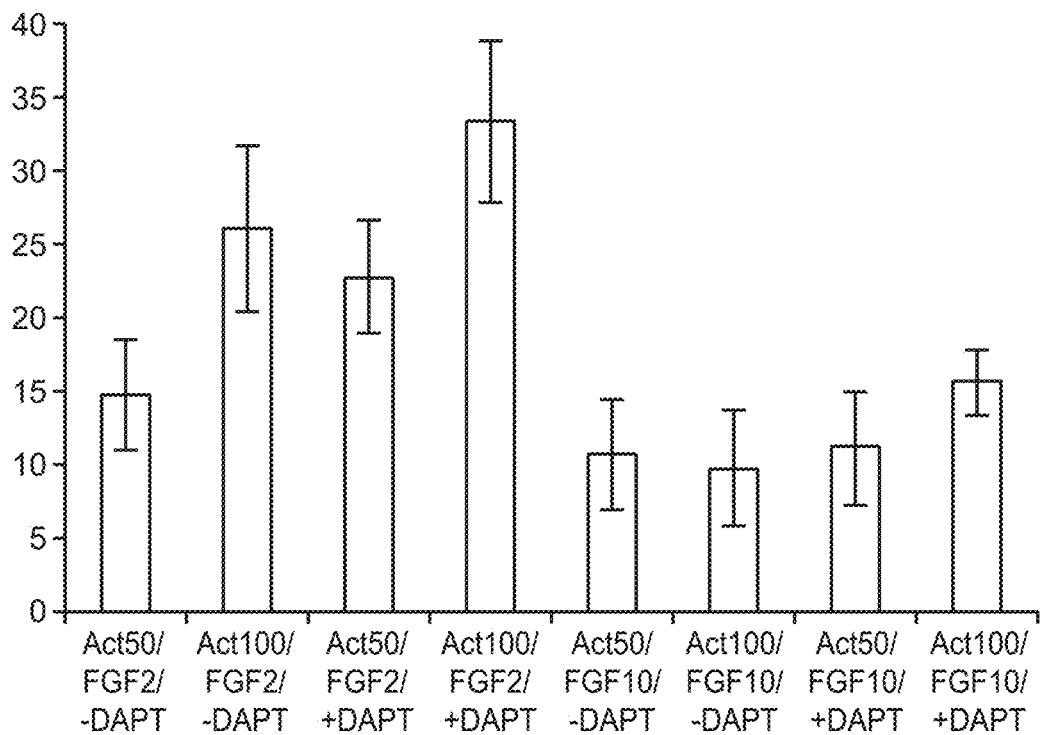
FIG. 6B

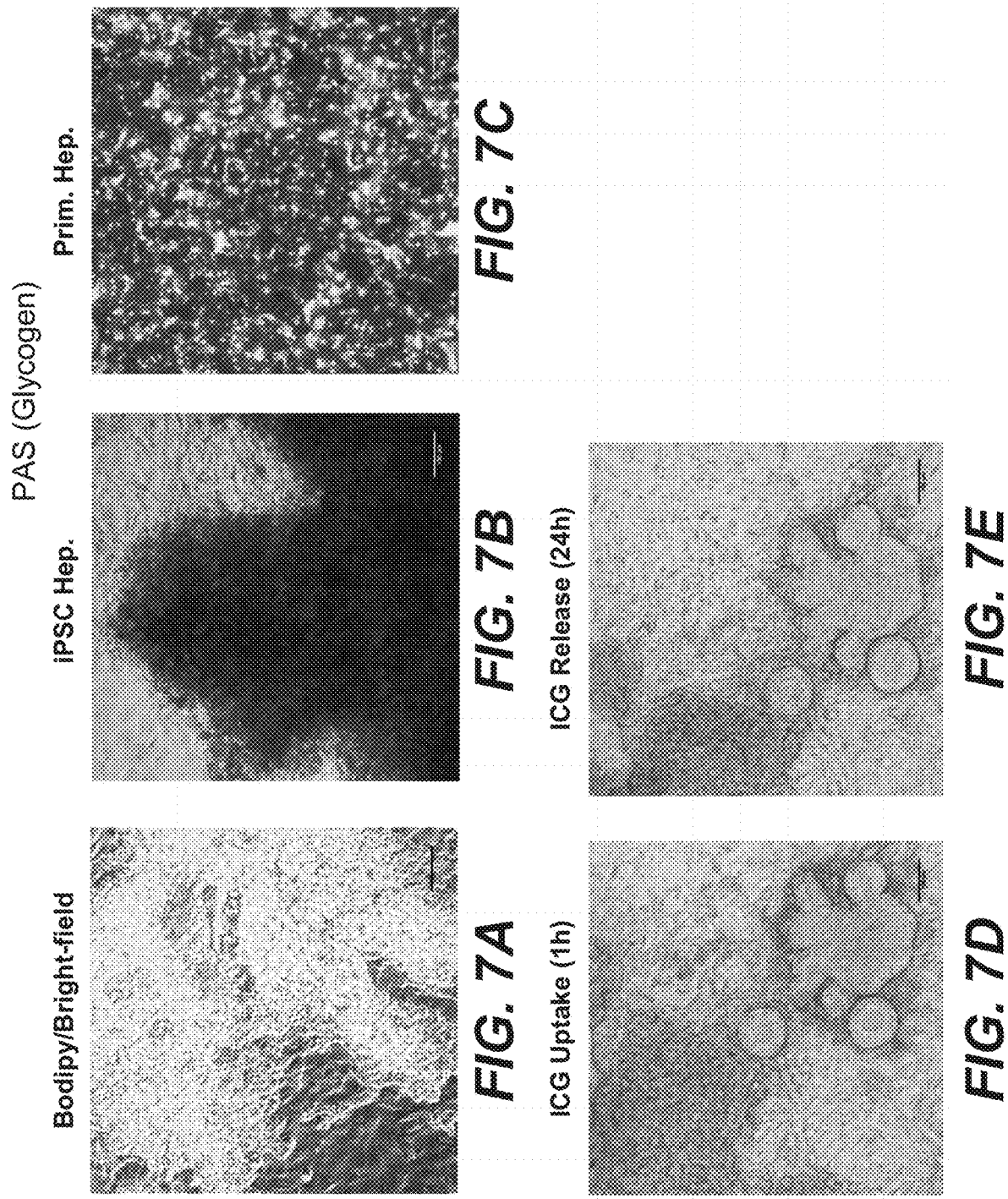

| Dissociation | Attachment | BF Day 23/Day 25 | ALB/Nuclei/BF Day 30 | |
|---|---|---|---|---|
| EDTA/PBS (3h) | No Hepatocytes | | | |
| GCD (3h) | No Hepatocytes | | | |
| Collagenase (o/n) | Few Hepatocytes | | | |
| Dispase (3h) + Trypsin 0.25% (1h) | No Cells | | | |
| Accutase (3h) | Hepatocytes | | | |
| Accutase (o/n) | No Cells | | | |
| Trypsin 0.05% (3h) | Hepatocytes | | | |
| Trypsin 0.25% (1h) | No Cells | | | |

*FIG. 9A*

NON-HUMAN PRIMATE INDUCED PLURIPOTENT STEM CELL DERIVED HEPATOCYTES AND USES THEREOF

CROSS-REFERENCE TO RELATED APPLICATION

This application is a continuation of International Application PCT/EP2017/068668, filed Jul. 24, 2017, which claims benefit of priority to European Application 16181715.0, filed Jul. 28, 2016, each of which is incorporated herein by reference in its entirety.

FIELD OF THE INVENTION

This application relates to non-human primate (NHP) induced pluripotent stem cell (IPSC)-derived hepatocytes and methods of producing the same. Moreover, this application relates to methods of using NHP IPSC-derived hepatocytes for drug screening, drug safety assessment and in models of infection.

BACKGROUND

Non-human primates (NHPs) are an important in vivo system for drug development to analyze the mode of action and potential toxicity of drug candidates. Because of their genomic and physiologic (e.g., drug metabolism, immune response) similarity to humans, NHPs are deemed especially relevant species for preclinical safety assessment. Unfortunately, in vitro systems for NHPs are largely limited to primary cells, the use of which is impeded by ethical constraints, and their limited availability and great variations between donors. Thus, in vivo studies are often deemed necessary.

As drug-induced liver injury (DILI) is one of the major causes for drug attrition, in vitro systems to evaluate DILI are of crucial impact for drug development. Additionally, in vitro liver models are necessary to effectively study life cycles of liver-specific pathogens, e.g., Hepatitis virus. Currently, primary hepatocytes are the gold standard of in vitro liver systems but their limited availability and donor-dependent variability in responsiveness to drugs limits their utility for certain applications.

Induced pluripotent stem cell (IPSC)-based in vitro models offer an unlimited supply of cells of a defined genetic background. Pluripotent stem cells (PSCs) are characterized by an unlimited proliferation capacity and the ability to differentiate into all cells of the body and can serve as a source for cells to establish in vitro models of tissues affected by adverse drug reactions (ADRs). While human IPSC-based liver models have been developed (Greenhough, Medine, Hay. Toxicology. 2010 Jul. 12; 278: 250-255), there is still a need for NHP IPSC-based liver models. Such cellular models would provide extremely useful tools to translate in vitro findings into in vivo applications which could potentially allow reduction of animal studies. Additionally, NHP-IPSC-based systems in combination with the corresponding human cells can be used to bridge the gap between preclinical and clinical research and allow earlier and better evaluation of drug candidates.

Efficient methods to derive hepatocytes from IPSCs have been developed for human cells, but not non-human primate cells. Few reports describe hepatic differentiation methods of NHP embryonic stem cells (Table 1). However, these methods suffer from low efficiency. Importantly, all of the previously described protocols are based on culture conditions using co-culture of ESCs with mouse feeder cells and non-defined media supplements, such as FCS, parameters with high variability that limit use of the resulting cells for drug screening.

TABLE 1

Hepatocyte differentiation of NHP stem cells: Overview over published studies.

| Reference | Starting cell type | Methods | Difference to present invention |
| --- | --- | --- | --- |
| Ma, Duan, Jung, Wu, VandeVoort, Zern. Cloning Stem Cells. 2008 Dec. 10; 4: 485-93. | Rhesus ESCs | No description in publication | feeder culture<br>no chemically defined medium<br>no IPSCs<br>no sorting/replating<br>low efficiency<br>(6.5% according to flow cytometry) |
| Tsukada, Takada, Shiomi, Torii, Tani. In Vitro Cell Dev Biol Anim. 2006 March-April; 42(3-4): 83-8 | Cynomolgus ESCs | Embyoid body formation followed by aFGF treatment | feeder culture<br>no chemically defined medium<br>EB based differentiation<br>no IPSCs<br>no sorting/replating<br>low efficiency<br>(0.9% ALB positive cells) |
| Kuai, Shao, Lu, Xiao, Zheng. J Dig Dis. 2014 January; 15(1): 27-34 | Rhesus ESCs | Embroid body differentiation (12 days) combined with growth factor treatment | feeder culture<br>no chemically defined media<br>EB based differentiation<br>no IPSCs<br>no sorting/replating<br>low efficiency (NA) |

Thus, there is a need for better methods of differentiating non-human primate IPSCs into hepatocytes to generate more relevant models for drug discovery, efficacy, and safety testing.

Specifically, there is a need for IPSC-derived hepatocytes under chemically-defined conditions with high efficiency and high purity. Further, there remains a need for methods of using these cells in in vitro models that can be adopted to various small and large scale culture formats suitable for drug screening and infectious disease modeling.

SUMMARY OF THE INVENTION

The novel method for differentiating NHP pluripotent stem cells, particularly induced pluripotent stem cells (IPSCs), into hepatocytes disclosed herein comprises linked steps of chemically defined media inductions, to produce NHP hepatocytes within about 28 days.

Accordingly, provided herein is a method for differentiating non-human primate (NHP) pluripotent stem cells into NHP hepatocytes, the method comprising the steps of:

a) providing NHP pluripotent stem cells in a feeder-free culture in a chemically defined medium;

b) contacting the pluripotent stem cells with a Wnt signalling activator to produce endodermal cells;

c) contacting the endodermal cells with BMP4 and a fibroblast growth factor to produce immature NHP hepatocytes; and d) contacting the immature NHP hepatocytes with HGF, OncostatinM and Dexamethasone to produce NHP hepatocytes.

In one embodiment the chemically defined medium is MT medium. MT medium comprises Dulbecco's Modified Eagle Medium with Ham's F12 Nutrient Mixture (DMEM/F12) with 2.5 mM GlutaMAX™, 7 µg/ml insulin, 450 µM monothioglycerole, 1× Lipid concentrate, 5 mg/ml BSA, 14 ng/ml sodium selenite, 1× non-essential amino acids, 2 mg/ml heparin, 15 µg/ml transferrin, and 220 µM ascorbic acid-2-phosphate.

In one embodiment the NHP pluripotent cells are provided in a chemically defined medium comprising FGF2 and ActivinA.

In one embodiment the NHP pluripotent stem cells are provided on growth-factor reduced MATRIGEL®.

In one embodiment the NHP pluripotent cells are provided at a density of about 45000 cells/cm$^2$.

In one embodiment the NHP pluripotent cells are provided at a density of 45000 cells/cm$^2$ on growth-factor reduced MATRIGEL®-coated plates in MT basic medium supplemented with 15 ng/ml FGF2, 10 ng/ml ActivinA and 10 µM Y-27632 (Rock-Inhibitor).

In one embodiment the medium is changed every day from day 1 to day 16 and thereafter every second day.

In one embodiment step b) and c) comprise contacting the cells with RPMI1640 comprising B27 and NEAA from day 3 to day 10 of differentiation.

In one embodiment the Wnt signalling activator is CP21. In one embodiment provided is a method as described herein, wherein step b) comprises contacting the cells with CP21 to induce differentiation.

In one embodiment provided is a method as described herein, wherein step b) comprises contacting the cells with Ly294002 and CP21 to induce differentiation.

In one embodiment provided is a method as described herein, wherein step b) comprises contacting the cells with a chemically defined medium comprising 100 ng/ml ActivinA, 10 µM Ly294002 and 1 µM CP21 on day 1.

In one embodiment provided is a method as described herein, wherein step b) comprises contacting the cells with LDN193189.

In one embodiment provided is a method as described herein, wherein step b) comprises contacting the cells with a chemically defined medium comprising 100 ng/ml ActivinA, 0.25 µM LDN193189 and 1 µM CP21 on day 2 and day 3 of differentiation.

In one embodiment provided is a method as described herein, wherein step b) comprises contacting the cells with a chemically defined medium comprising 50 ng/ml or 100 ng/ml ActivinA on day 4 of differentiation.

In one embodiment provided is a method as described herein, wherein step b) comprises contacting the cells with knock-out serum replacement (KSR) and DMSO.

In one embodiment provided is a method as described herein, wherein step b) comprises contacting the cells with a chemically defined medium comprising 50 ng/ml or 100 ng/ml ActivinA, 2% knock-out serum replacement (KSR) and 0.5% DMSO on day 5 and day 6 of differentiation.

In one embodiment provided is a method as described herein, wherein the fibroblast growth factor of step c) is FGF2 or FGF10.

In one embodiment provided is a method as described herein, wherein step c) comprises contacting the cells with BMP4, DMSO and FGF2 or FGF10.

In one embodiment provided is a method as described herein, wherein step c) comprises contacting the cells with a chemically defined medium comprising 2% KSR, 10 ng/ml BMP4, 10 ng/ml FGF2 or FGF10 and 0.5% DMSO from day 7 to day 10 of differentiation.

In one embodiment provided is a method as described herein, wherein step d) comprises contacting the cells with a chemically defined medium comprising 20 ng/ml HGF, 20 ng/ml Oncostatin M, 100 nM dexamethasone and 0.5% DMSO from day 11 to day 28 of differentiation.

In one embodiment provided is a method as described herein, wherein step d) comprises contacting the cells with DAPT.

In one embodiment provided is a method as described herein, wherein step d) comprises contacting the cells with a chemically defined medium comprising 1 µM DAPT from day 11 to day 15 of differentiation.

In one embodiment provided is a method as described herein, wherein step d) comprises changing the chemically defined medium to HBM medium comprising Single-Quots™ (Lonza) from day 11 to day 28 of differentiation.

In one embodiment the cells take up and release rifampicin indicating the presence of hepatocyte specific transporter proteins.

In one embodiment the NHP hepatocytes upregulate metabolic enzymes. In one embodiment the metabolic enzymes are CYP450 enzymes.

In one embodiment the NHP hepatocytes comprise lipid vesicles.

In one embodiment the NHP hepatocytes express at least one hepatic marker selected from the group consisting of AFP, ALB and αIAT. In one embodiment expression of at least one hepatic marker is determined by immunostaining.

In one embodiment the NHP hepatocytes take up and release indocyanin green in an in vitro assay.

In one embodiment the NHP hepatocytes express CYP450 enzymes. In one embodiment expression of CYP450 enzymes is determined by mRNA expression.

In one embodiment the NHP pluripotent stem cells of step a) are induced pluripotent stem cells (IPSCs).

In one embodiment the NHP pluripotent stem cells are derived from a species selected from the group consisting of Cynomolgus monkey (*Macaca fascicularis*) and Rhesus monkey (*Macaca mulatta*). In one embodiment the NHP pluripotent stem cells are derived from Cynomolgus monkey (*Macaca fascicularis*).

In one embodiment provided is a feeder-free NHP hepatocyte culture in a chemically defined medium. In one embodiment provided is a feeder-free NHP hepatocyte culture in a chemically defined medium, wherein the species is Cynomolgus monkey.

In one embodiment provided is a NHP hepatocyte obtained by a method as described herein. In one embodiment provided is a Cynomolgus monkey hepatocyte obtained by a method as described herein.

In one embodiment provided is a biobank of NHP hepatocytes obtained by a method as described herein.

Yet another aspect of the invention is the use of the NHP hepatocytes obtained by a method as described herein or of the biobank as described herein as in vitro model for diseases caused by dysfunction of liver cells.

Yet another aspect of the invention is the use of the NHP hepatocytes obtained by a method as described herein or of the biobank as described herein as in vitro model for infection of liver cells. In yet another aspect of the invention the infection is selected from the group consisting of viral infection, bacterial infection, fungal infection, or parasitic infection. In yet another aspect of the invention the viral infection is selected from the group consisting of Hepatitis A virus infection, Hepatitis B virus infection, Hepatitis C virus infection, Eppstein Barr virus infection. In yet another aspect of the invention the viral infection is a Hepatitis B virus infection.

In one embodiment provided is a method for testing the potential toxicity of a compound, the method comprising the steps of: (i) exposing one or more NHP hepatocytes prepared as described herein to the compound; and (ii) monitoring the one or more mature NHP hepatocytes for signs of toxicity.

In one embodiment provided is a method for testing the potential toxicity of a compound, the method comprising the steps of: (i) exposing one or more NHP hepatocytes prepared as described herein to the compound, whereby the compound is metabolized by the NHP hepatocytes; (ii) contacting the resulting metabolite of the compound with one or more non-hepatocyte cells; and (iii) monitoring the one or more non-hepatocyte cells for any metabolite-induced changes.

In one embodiment provided is an in vitro method for supporting the replication of a virus, the method comprising the step of exposing one or more NHP hepatocytes prepared as described herein to the virus, wherein the virus replicates within the one or more NHP hepatocytes.

One aspect of the invention is the use of any of the cells described herein for in vitro testing of toxicity of a compound.

A further aspect of the invention is the use of any of the cells described herein as in vitro infection model of a virus.

In one embodiment provided is a method of preparing an in vitro non-human primate hepatocyte assay, the method comprising the steps of:

i) providing NHP hepatocytes prepared by the method as described herein;

ii) contacting the NHP hepatocytes for between about 1 and about 3 hours with Accutase to detach the NHP hepatocytes;

iii) replating the detached NHP hepatocytes in a suitable assay format.

In a further embodiment the detached NHP hepatocytes are enriched for SCARB1-positive cells before replating. In yet a further embodiment the cells are enriched using fluorescence activated or magnetic activated cell sorting (FACS or MACS). In yet a further embodiment the NHP hepatocytes are replated onto laminin, collagen or matrigel. In yet a further embodiment the NHP hepatocytes are replated as a matrigel sandwich culture.

Any of the above embodiments may be present singly or in combination.

SHORT DESCRIPTION OF THE FIGURES

FIG. 1A-FIG. 1E show quality control of NHP-IPSCs using immunofluorescence staining of pluripotency markers OCT4 (FIG. 1A), SOX2 (FIG. 1B) and NANOG (FIG. 1C) and the neural marker SOX1 (FIG. 1D) in cynomolgus IPSCs. The table (FIG. 1E) shows the percentage of positive cells.

FIG. 2 illustrates the experimental design to test media combinations for hepatocyte differentiation. Basic media contained either MT or RPMI medium for differentiation and either MT or HBM medium for maturation, resulting in the conditions I MT/MT, II MT/HBM, III RPMI/HBM and IV RPMI/MT. Supplements are depicted in grey boxes and were the same for all basic media.

Figure 3A:
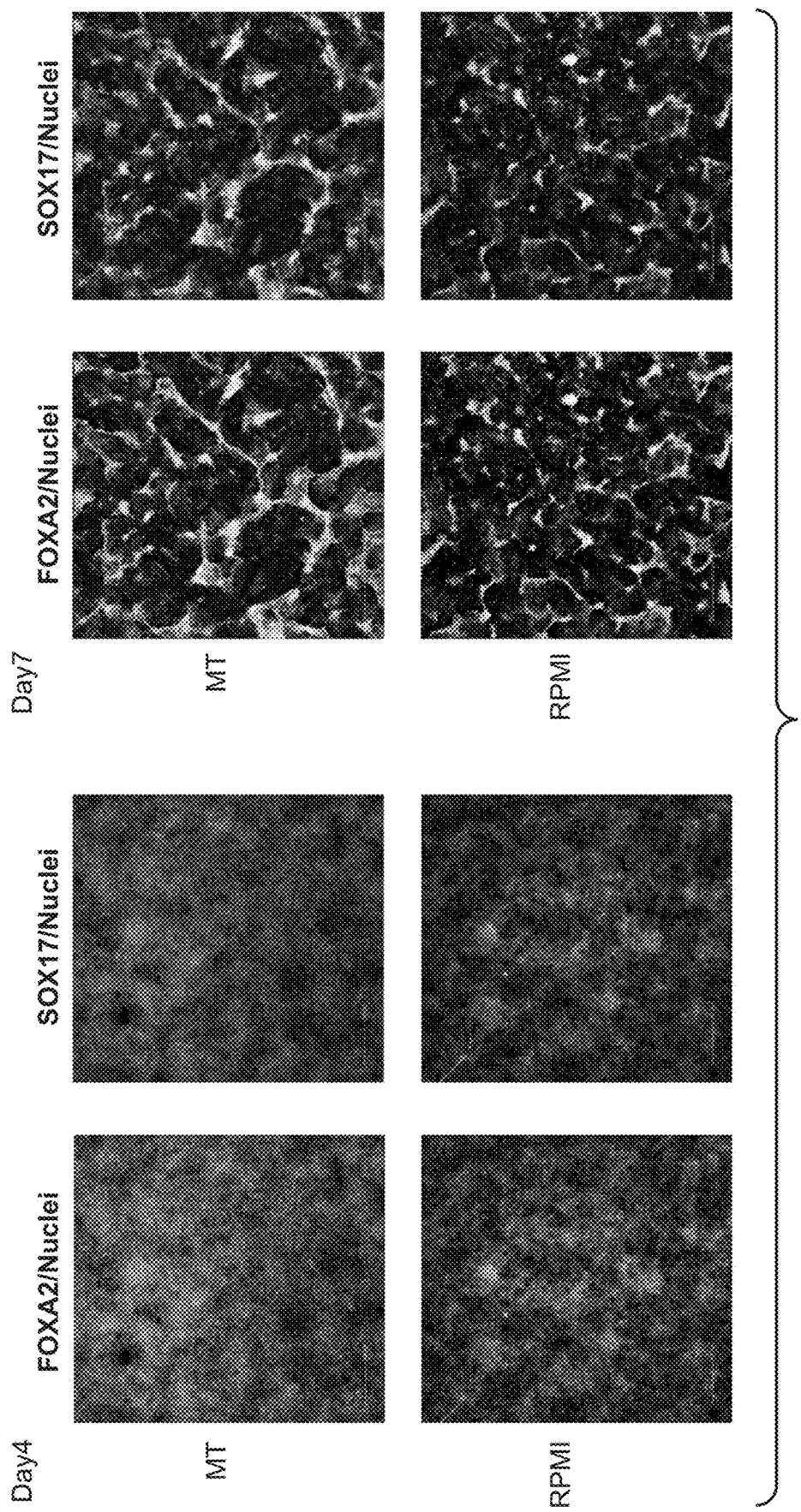
Figure 3B:
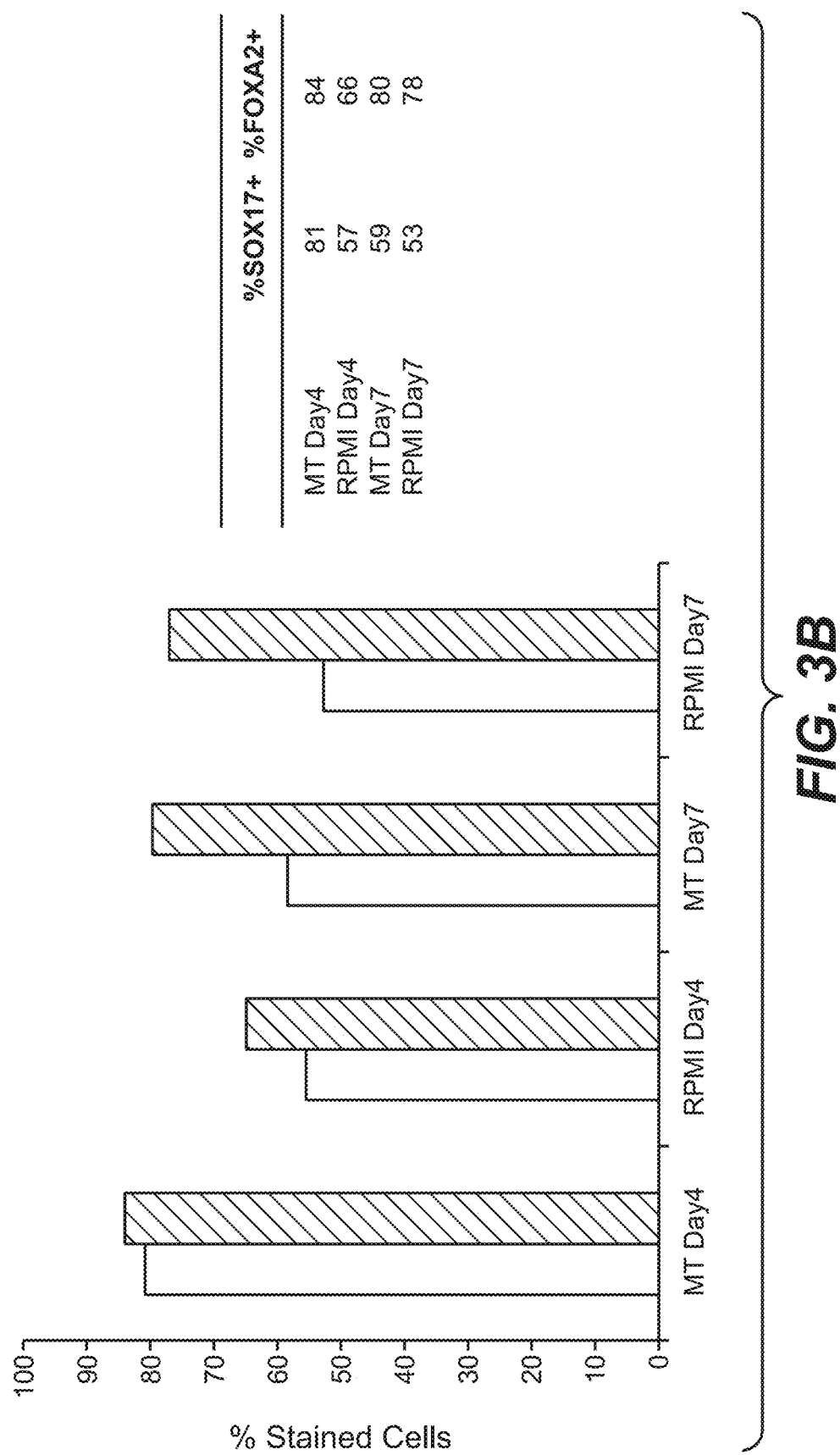

FIG. 3A-FIG. 3B show the results of the evaluation of different media compositions on endoderm induction in NHP-IPSCs. FIG. 3A: Immunofluorescence staining of definitive endoderm markers FOXA2 and SOX17 on day 4 and day 7 of differentiation in MT (top) and RPMI (bottom) media. FIG. 3B: Quantification of FoxA2 (shaded bars)/Sox17 (open bars) positive cells.

Figure 4A:
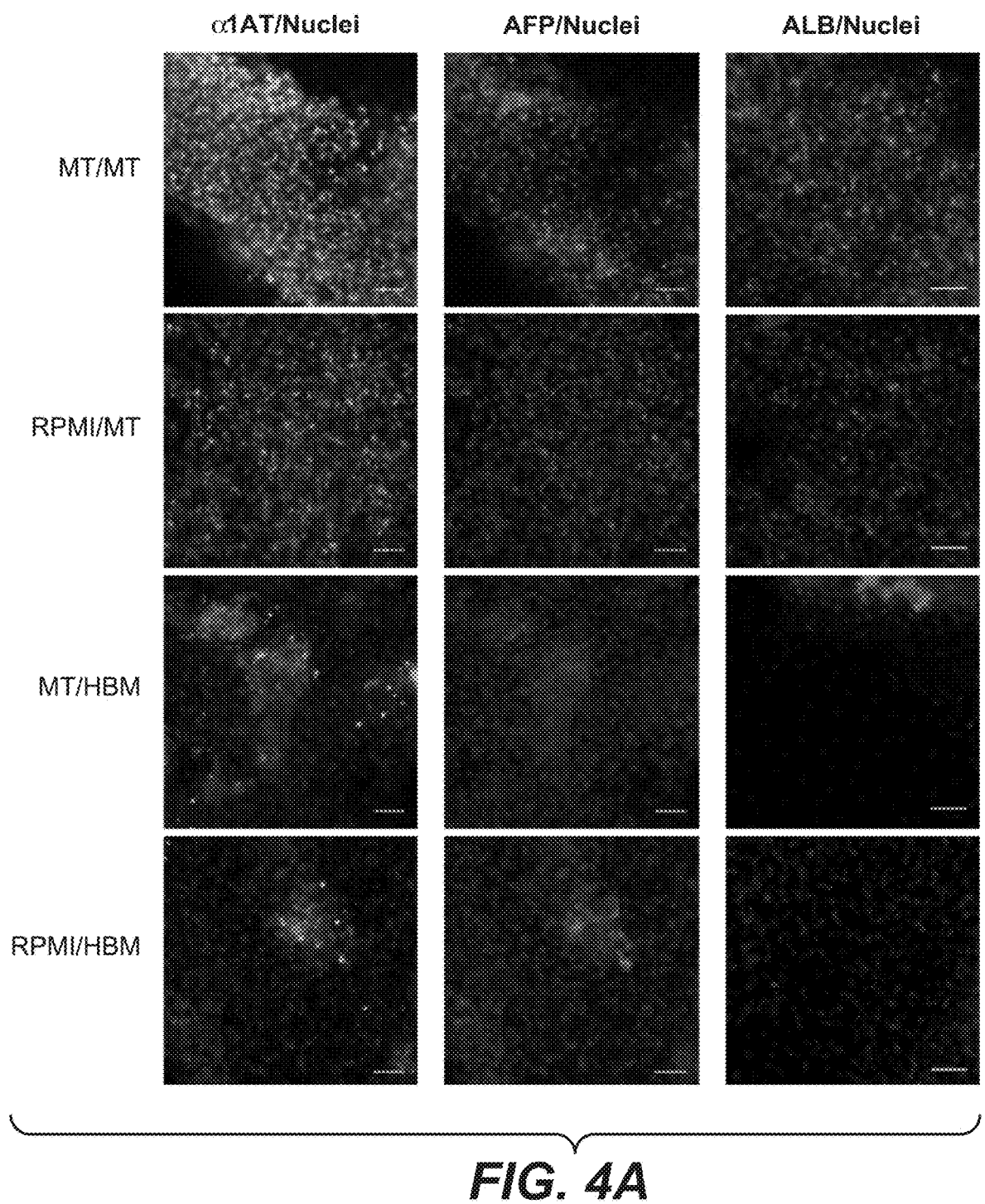
Figure 4B:
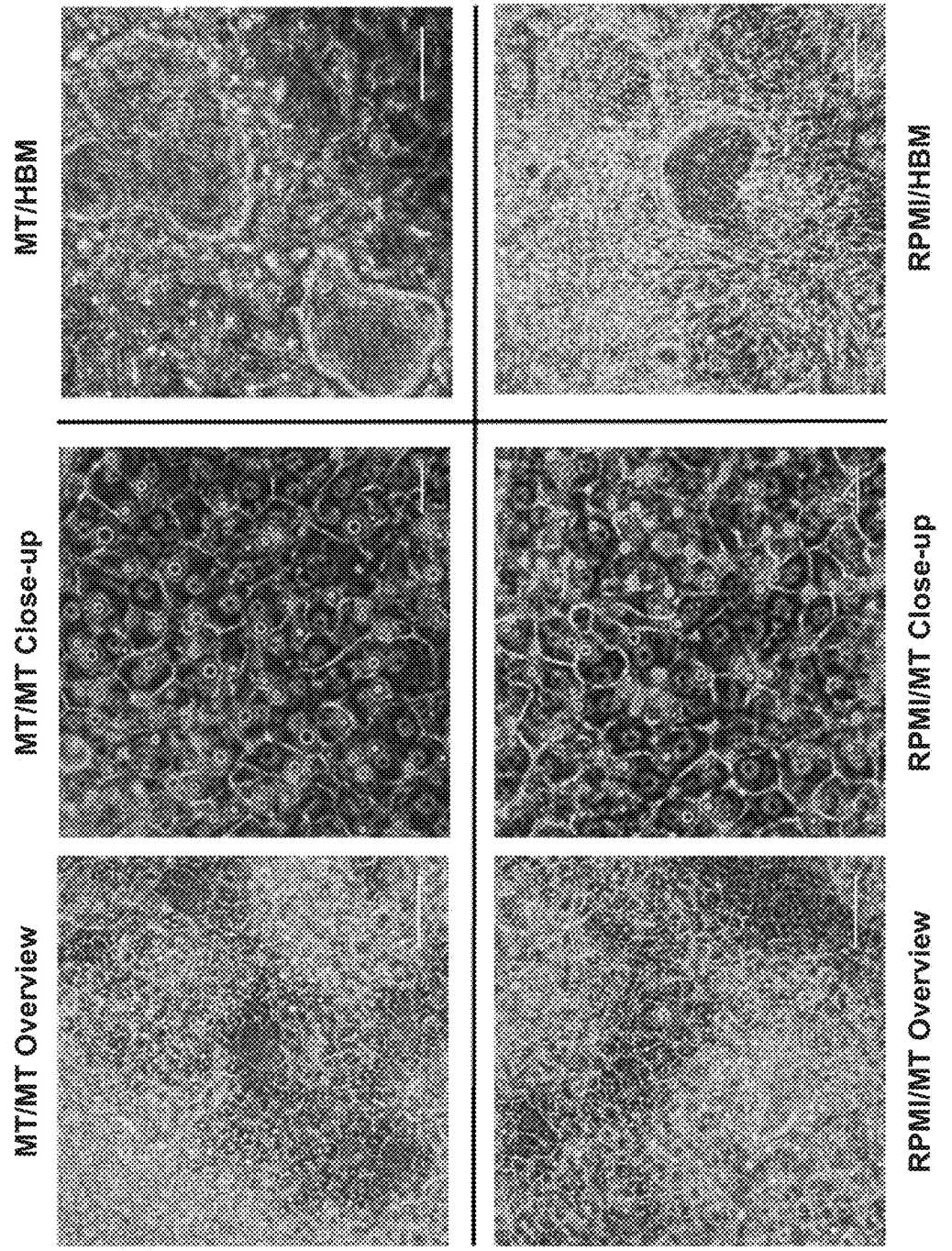

FIG. 4A-FIG. 4B show the impact of various media compositions on hepatocyte differentiation and maturation. FIG. 4A: Immunofluorescence staining at day 15 of differentiation for α1AT and AFP, and ALB on day 21. Scale bar is 50 μm. FIG. 4B: Hepatocyte morphology on day 21 of differentiation. Overviews show large areas of hepatocytes, close-up pictures show a characteristic hepatocyte morphology of cells with cobblestone shape and large round nuclei. Differentiation in MT/HBM or RPMI/HBM medium did not yield to hepatocytes. Scale bar for overview images of MT/MT, RPMI/MT and RPMI/HBM is 100 μm, for MT/HBM 50 μm and for close-up images MT/MT and RPMI/MT 20 μm.

Figure 5:
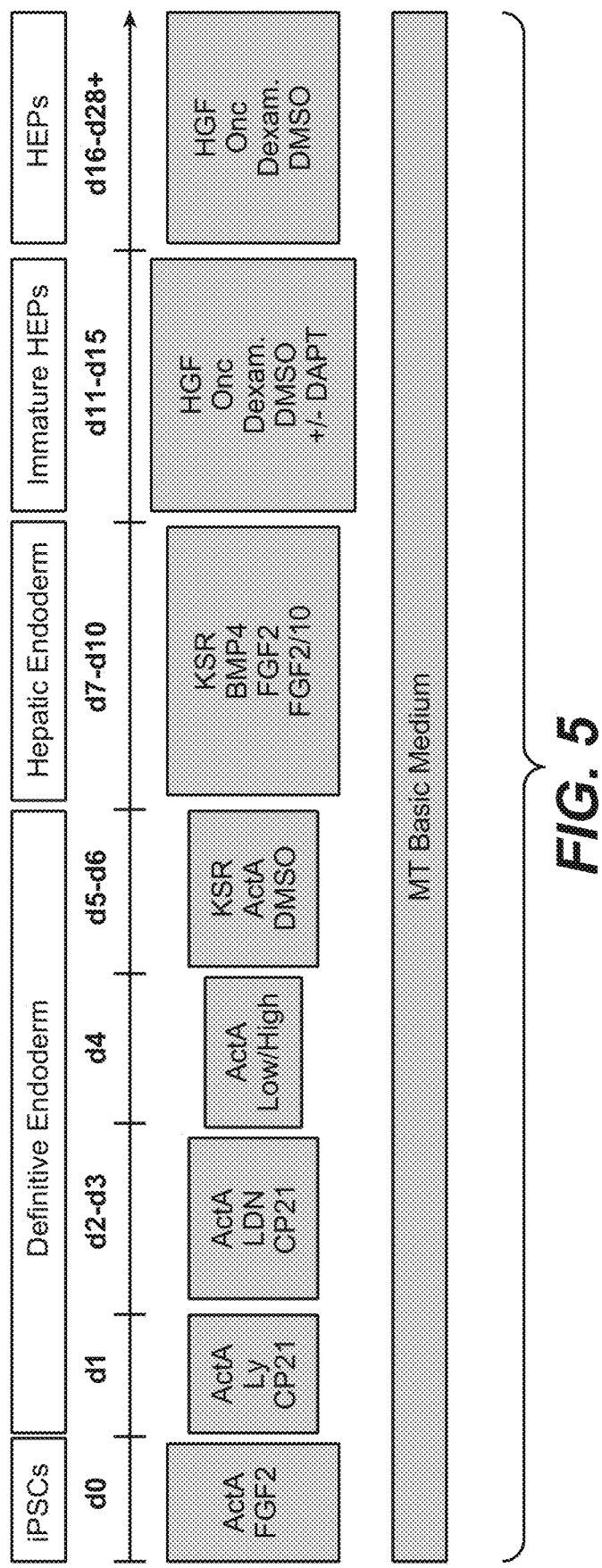

FIG. 5 illustrates an overview of the parameters tested to optimize hepatocyte differentiation. MT basic medium was supplemented with growth factors and small molecules indicated in the grey boxes of the respective time frame. The red marked substances were varied resulting in 8 different media compositions. ActA low indicates a concentration of 50 ng/ml and ActA high of 100 ng/ml.

FIG. 6A-FIG. 6B show the effects of various parameters on efficiency of hepatocyte differentiation. FIG. 6A: Immunostaining for ALB at day 21. Images show triplicates of each condition. Scale bar is 10 mm. FIG. 6B: Quantification of hepatocyte formation. ALB stained area or area covered with cells with hepatocyte morphology were quantified. Columns represent mean+/−SD of three biological replicates.

FIG. 7A-FIG. 7E show characterization of NHP-IPSC derived hepatocytes. FIG. 7A: Lipid storage visualized by BODIPY staining. FIG. 7B and FIG. 7C: Glycogen storage visualized by PAS staining. Primary cynomolgus hepatocytes were used as positive control. FIG. 7D and FIG. 7E: Uptake and release of indocyanine green (ICG) indicating presence of hepatocyte specific transporter proteins. Scale bars: 100 μm.

Figure 8A:
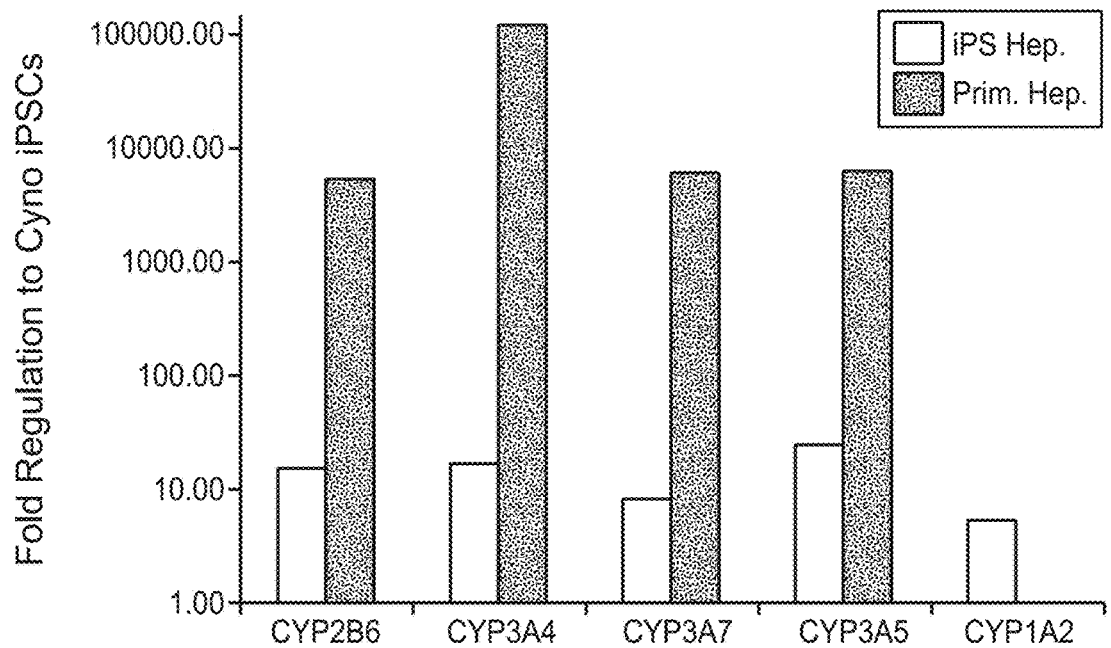
Figure 8B:
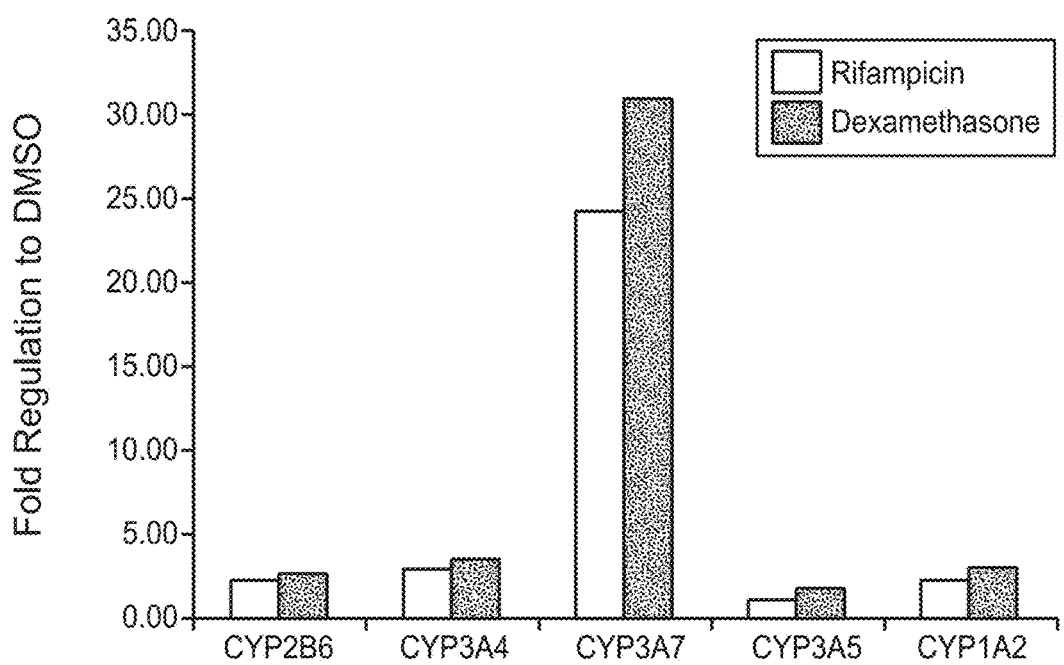
Figure 8C:
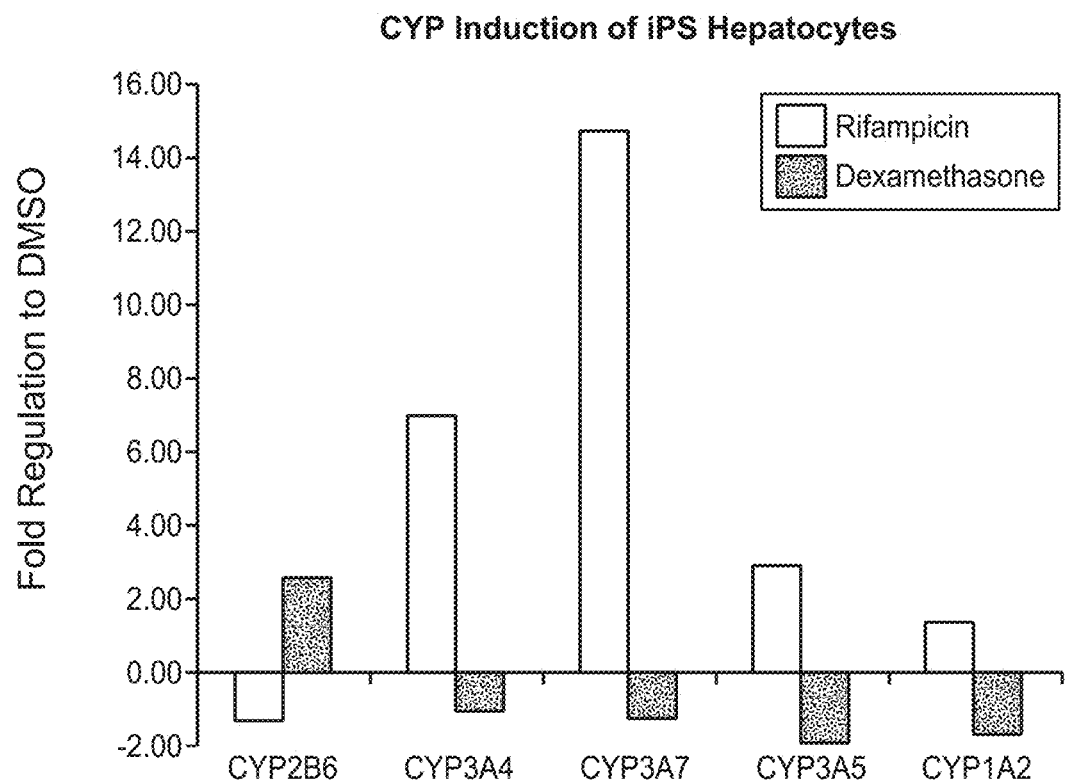
Figure 8D:
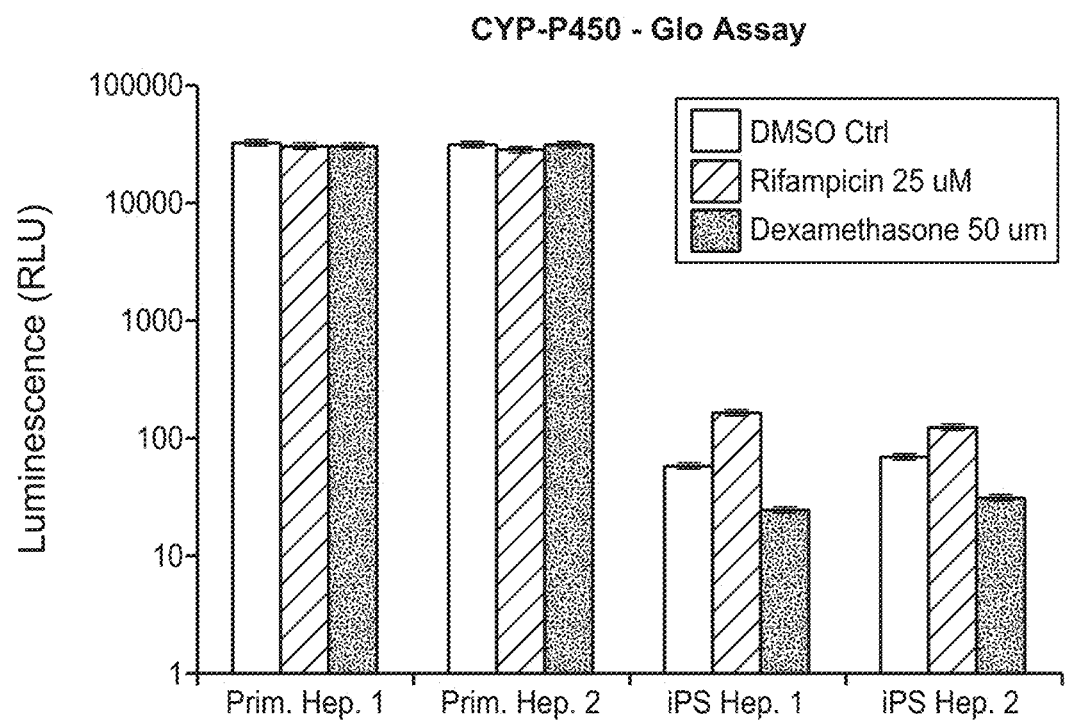

FIG. 8A-FIG. 8D show expression of enzymes of the CYP-P450 family in IPSC-derived hepatocytes and primary hepatocytes. FIG. 8A-FIG. 8C: mRNA expression levels determined by quantitative real-time PCR. Graphs show fold regulation to undifferentiated IPSCs (FIG. 8A) or to cells treated with DMSO (FIG. 8B and FIG. 8C). Bars represent the average of technical triplicates. Expression was normalized to the house-keeping gene GAPDH. FIG. 8D: CYP-P450 enzyme activity of IPSC-derived hepatocytes and primary hepatocytes measured by luminescence of proluciferin-coupled CYP3A4 substrates which are converted to fluorescent luciferin by active CYP enzymes. Two biological replicates were measured. Cells were incubated with rifampicin or dexamethasone for 24 hours to analyze induction of CYP-P450 enzymes compared to cells incubated with DMSO. Bars represent average of technical triplicates+/− standard deviation.

Figure 9B:
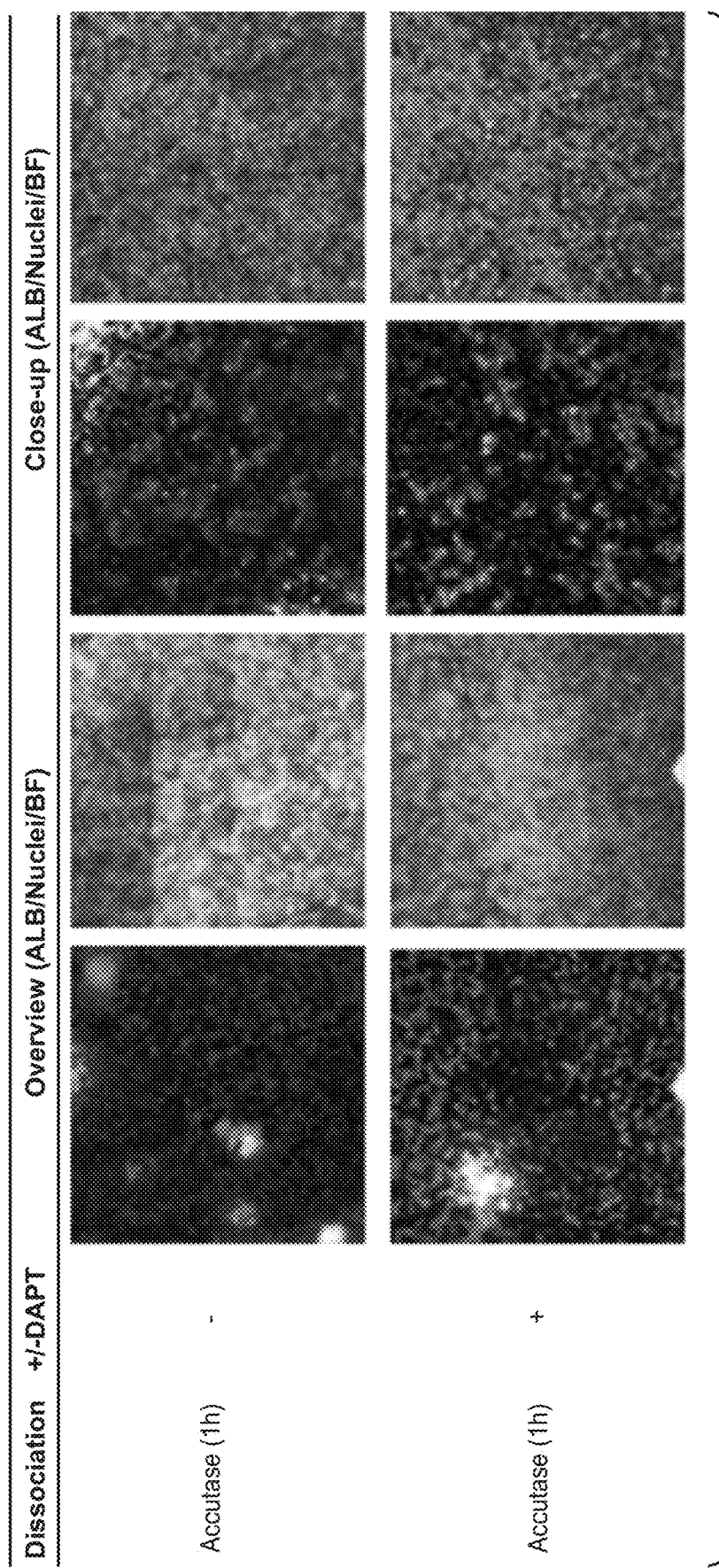

FIG. 9A-FIG. 9B show defining conditions allowing replating of differentiated hepatocytes. FIG. 9A: Feasibility of various dissociation reagents to replate cells on day 21. Bright-field (BF) images taken on day 23 or day 25 of differentiation showed attachment of the cells, immunofluorescence staining for ALB on day 30 of differentiation showed hepatocytes after replating. Scale bars: 100 µm. FIG. 9B: Refinement of Accutase treatment for replating. IPSC-derived cells differentiated with/without DAPT addition.

Figure 10:
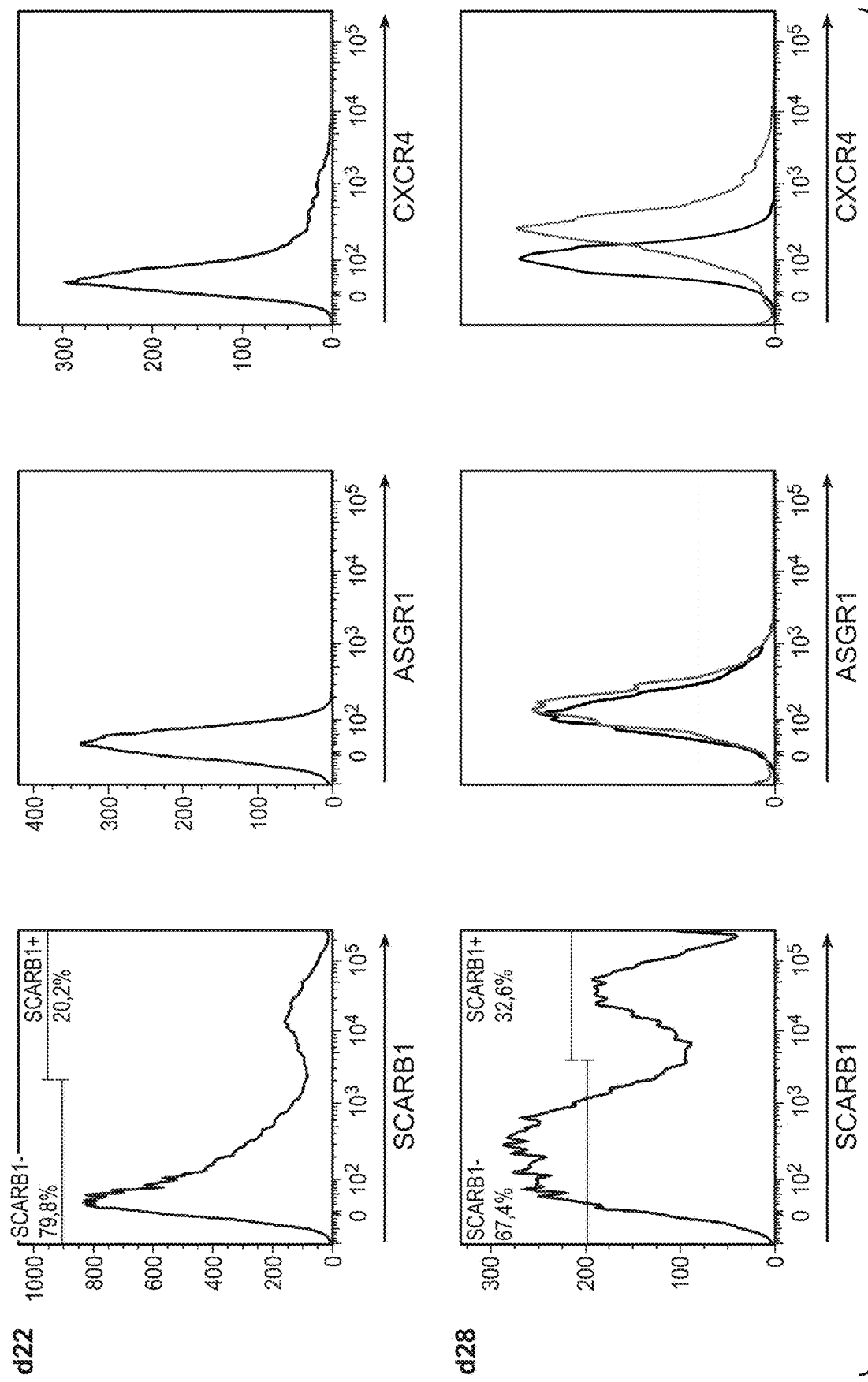

FIG. 10 shows expression of hepatocyte-specific cell surface markers during differentiation of NHP-IPSCs. Flow cytometry analysis at day 22 (top) and day 28 of differentiation. The fact that ASGR expression cannot be detected might be due to lacking species cross-reactivity of the antibody.

Figure 11A:
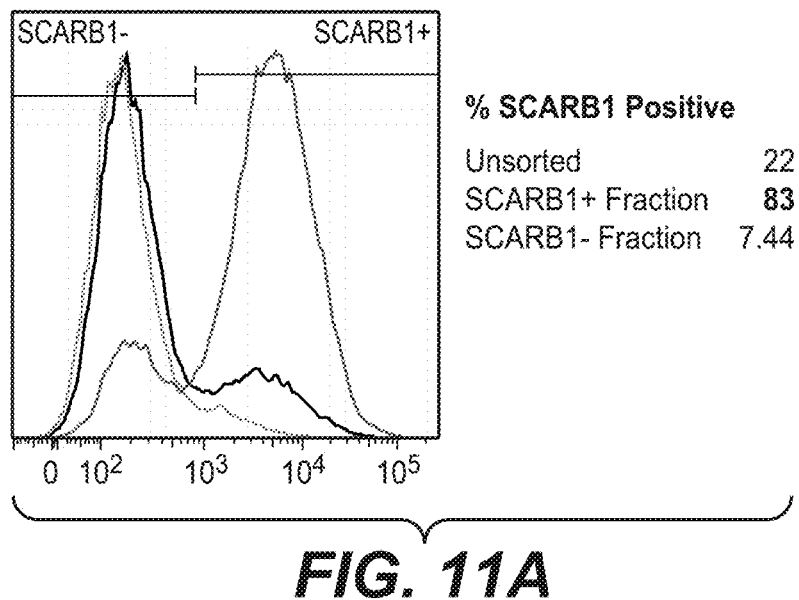
Figure 11B:
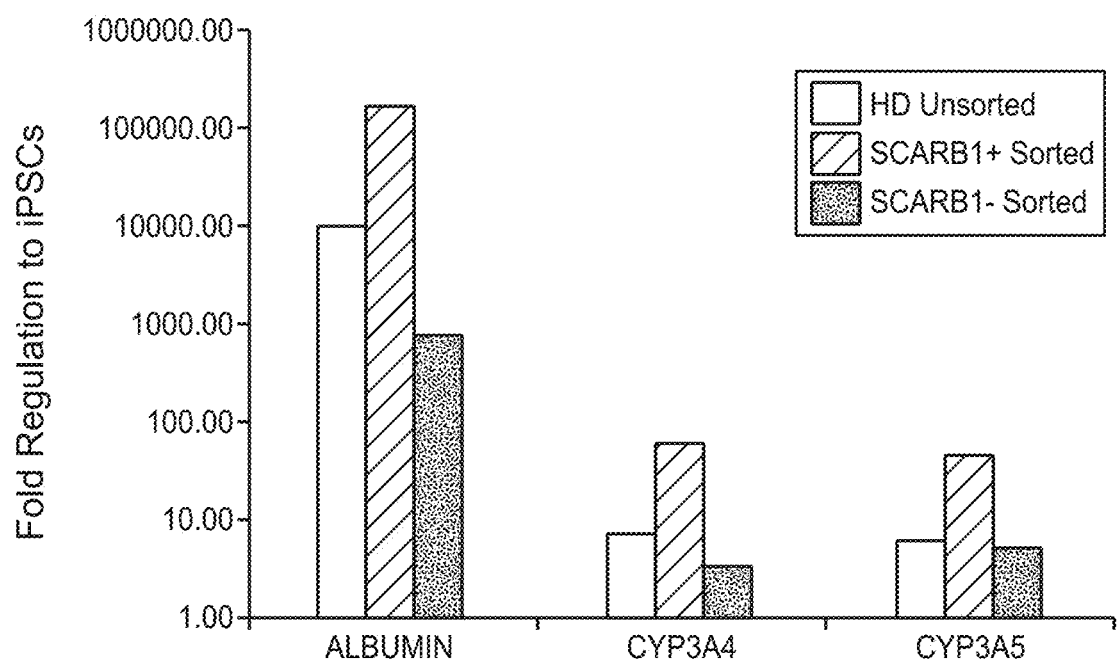
Figure 11C:
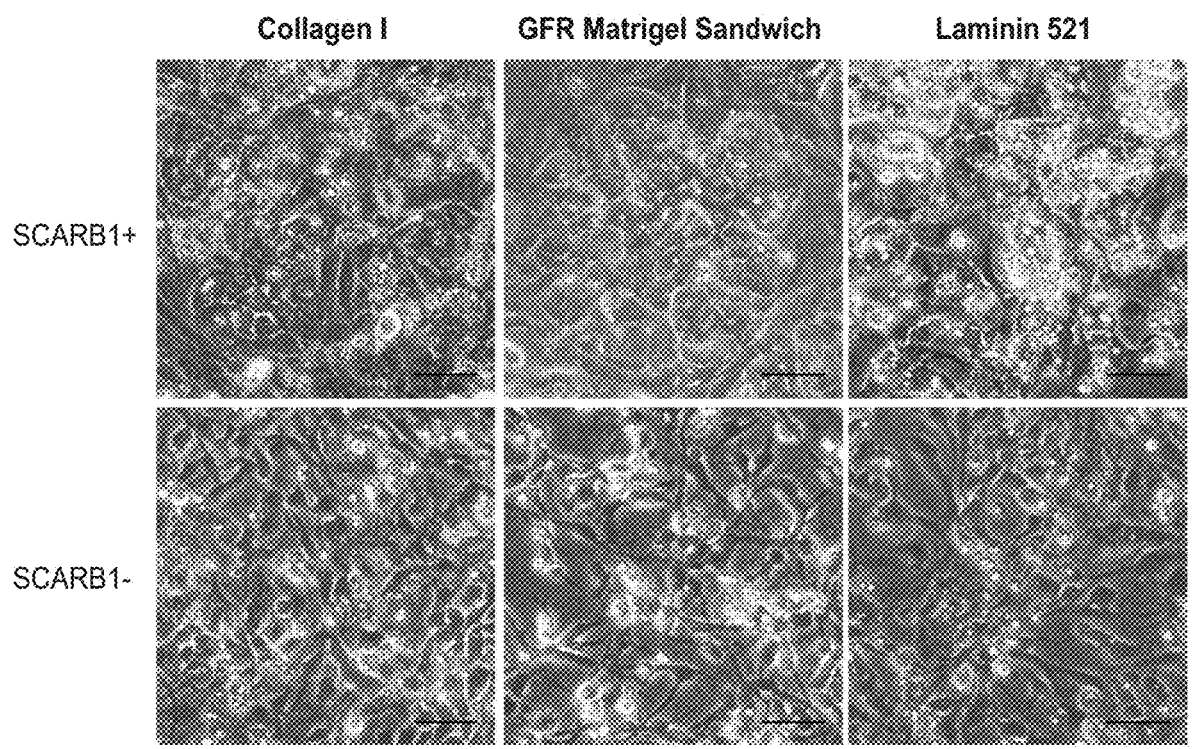

FIG. 11A-FIG. 11C show enrichment of NHP-IPSC derived hepatocytes using MACS sorting for SCARB1 positive cells. FIG. 11A: Flow cytometry analysis before and after sorting. FIG. 11B: mRNA expression of hepatocyte markers in unsorted, SCARB1+ and SCARB1− cells. FIG. 11C: Phase contrast images of sorted cells demonstrates enrichment of hepatocytes in SCARB1+ fraction. Scale bars: 50 µm.

Figure 12:
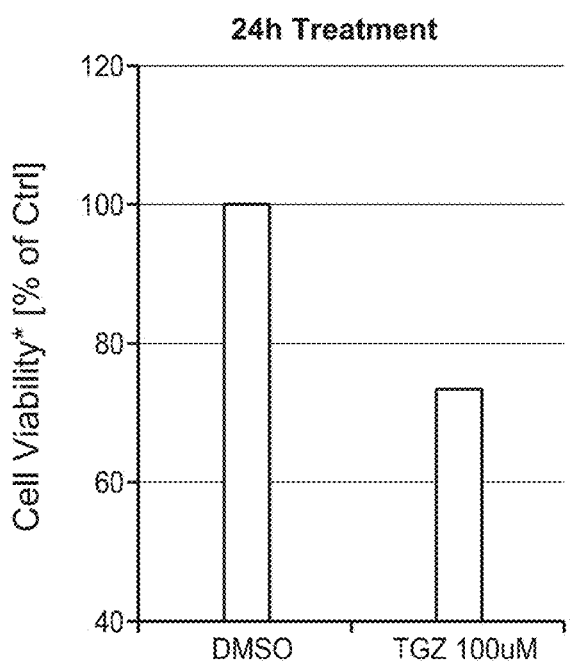

FIG. 12 shows application of NHP-IPSC-derived hepatocytes to evaluate hepatotoxicity in vitro. Cells were treated for 24 hours with the hepatotoxic compound Troglitazone and cell viability was assessed using WST1 assay. Columns show mean of two biological replicates.

DETAILED DESCRIPTION

As used herein, the term "defined medium" or "chemically defined medium" refers to a cell culture medium in which all individual constituents and their respective concentrations are known. Defined media may contain recombinant and chemically defined constituents.

As used herein the terms "differentiating" and "differentiation" refers to one or more steps to convert a less-differentiated cell into a somatic cell, for example to convert a pluripotent stem cell into a hepatocyte. Hepatocytes derived from human IPSCs can be generated according to protocols known in the art (see e.g., Hannan, Segeritz, Touboul, Ludovic. Nature Protocols. 2013; 8: 430-437). Differentiation of a NHP PSCs, in particular NHP IPSCs, into NHP hepatocytes is achieved by the method described herein.

"Expression of marker" means that a certain gene is transcribed into mRNA and usually is subsequently translated into a protein (its gene product) which exerts a certain function in a cell. The expression of a marker can be detected and quantified on the RNA level or on the protein level by methods known in the art. Preferred herein is the detection of the expression of a marker on the protein level, e.g., by testing for the presence of a certain protein with antibodies binding to the marker. "Expression markers" can be used to determine the identity of a cell type. PSC cell markers are known in the art and may e.g., comprise Ecat1, Esg1, Nanog, Eras, Gdf3, Fgf4, Cripto, Cax1, Zfp296, Slc2a3 and Nat1, Oct4 and Sox2.

As used herein, the term "feeder free" refers to cell culture that does not employ the use of feeder cultures. Feeders are cells of a different cell type and/or from a different species as the cells to be cultured that serve to provide nutritional and/or structural support for the cultured cells. Examples of feeder cultures are mouse embryonic fibroblasts (MEFs). As an example, a feeder-free NHP hepatocyte culture is free of feeder cells, e.g., MEFs. The absence of feeder cells can be determined according to methods known in the art, e.g. by measuring feeder cells specific gene expression by real time PCR.

The term "hepatocyte" or "HEP" as used herein refers to a cell which is similar to or identical to a cell of the main parenchymal tissue of the liver. Likewise, the term "NHP hepatocyte" or "NHP HEP" refers to a non-human primate hepatocyte or non-human PSC-derived hepatocyte. The term "immature hepatocyte" as used herein refers to a cell which is more similar to a fetal hepatocyte regarding its marker expression (e.g., AFP expression instead of ALB) but which expresses markers associated with cellular and/or metabolic functions of hepatocytes and which adopts a hepatocyte cell shape as described herein.

As used herein, the term "hepatocyte maturation medium" refers to a defined medium that comprises MT medium supplemented with 20 ng/ml HGF, 20 ng/ml Oncostatin M, 100 nM dexamethasone and 0.5% DMSO.

"High-throughput screening" as used herein shall be understood to mean that a relatively large number of different disease model conditions and/or chemical compounds can be analyzed and compared with the novel assay described herein. Typical such high-throughput screening is performed in multi-well microtiter plates, e.g., in a 96 well plate or a 384 well plate or a plates with 1536 or 3456 wells.

As used herein, the term "MT medium" or "MT basal medium" or "MT basic medium" refers to a defined medium that contains Dulbecco's Modified Eagle Medium with Ham's F12 Nutrient Mixture (DMEM/F12) with 2.5 mM GlutaMAX™, 7 µg/ml insulin, 450 µM monothioglycerole, 1× Lipid concentrate, 5 mg/ml BSA, 14 ng/ml sodium selenite, 1× non-essential amino acids, 2 mg/ml heparin, 15 µg/ml transferrin, and 220 µM ascorbic acid-2-phosphate.

As used herein, the term "MT complete medium" refers to MT medium that contains 15 ng/ml bFGF (FGF2) and 10 ng/ml ActivinA.

The term "non-human primate" or "NHP" as used herein refers to species belonging to the order of primates with the exception of *Homo sapiens*. In particular, NHP species according to the methods disclosed in the present invention include but are not limited to *Pan troglodytes, Pan paniscus, Hylobates lar, Gorilla gorilla, Pongo abelii, Pongo pygmaeus, Cercopithecus mitis, Cercopithicus neglectus, Chlorocebus aethiops, Chlorocebus sabaeus, Colobus guereza, Lophocebus aterrimus, Macaca arctoides, Macaca assamensis, Macaca fascicularis, Macaca fuscata, Macaca mulatta, Macaca nemestrina, Macaca silenus, Mandrillus leucophaeus, Mandrillus sphinx, Macaca thibetana, Papio anubis, Papio cynocephalus, Papio hamadryas, Papio papio, Papio ursinus, Presbytis entellus, Theropithecus gelada, Aotus azarae, Aotus nancymaae, Aotus nigriceps, Aotus trivirgatus, Aotus vociferans, Ateles belzebuth, Ateles fusciceps, Callithrix jacchus, Callicebus moloch, Cebuella pygmaea, Cebus apella, Leontopithecus rosalia, Pithecia pithecia, Saguinus fuscicollis, Saguinus geoffroyi, Saguinus labiatus, Saguinus mystax, Saguinus oedipus, Saimiri sciureus.*

"Pluripotency medium" as used herein refers to any chemically defined medium useful for the attachment of the NHP pluripotent stem cells as single cells while maintaining their pluripotency and are well known in the art.

The term "stem cell" as used herein refers to a cell that has the ability for self-renewal and differentiation. An "undifferentiated stem cell" as used herein refers to a stem cell that has not undergone differentiation. As used herein, "pluripotent stem cells" or "PSC" refers to stem cells that can give rise to cell types of the three germlayers (endoderm, ectoderm, mesoderm) as well as the germline. Pluripotent stem cells (PSCs) include but are not limited to "NHP embryonic stem cells" ("NHP ESCs") and "NHP induced pluripotent stem cells" ("NHP IPSCs").

The term "sorting" or "cell sorting" as used herein refers to separating various cells of a cell population based on their properties such as cell surface marker expression.

The present disclosure relates generally to non-human primate (NHP) pluripotent stem cell-derived hepatocytes and methods of producing the same. The disclosure further relates to use of these NHP hepatocytes for in vitro drug screening, safety assessment and models of infection.

Prior studies reported hepatocyte differentiation of NHP embryonic stem cells (Table 1). In general, these strategies are based on feeder-cultured stem cells and differentiation methods using embryoid body formation and chemically undefined media. All of these parameters render the resulting cells unsuitable for drug development due to high variability and introduction of undefined factors. Furthermore, current attempts to differentiate NHP stem cells into hepatocytes suffer from low efficiencies and do not provide strategies to enrich and replate NHP hepatocytes in formats suitable for drug candidate screening applications.

Presented herein are robust and efficient methods to derive hepatocytes from NHP pluripotent stem cells (PSCs), in particular NHP induced pluripotent stem cells (IPSCs). Further, the inventors developed strategies for sorting and replating the obtained NHP hepatocytes which are prerequisites for using the NHP hepatocytes as in vitro screening model in drug development. Moreover, the data presented herein demonstrate that the NHP hepatocytes obtained by the method of the invention are suitable for use as in vitro models to assess drug induced liver injury or to model infections with primate-specific pathogens.

This system provides a valuable tool for drug development as it represents the first NHP in vitro system that does not require sacrifice of animals. Moreover, it allows analysis of NHP responsiveness to pathogens or drugs prior to in vivo studies enabling prioritization of drug candidates. As the corresponding human hepatocytes are available, NHP hepatocytes obtained by the methods as described herein can be used for inter-species comparison and more precise translation of preclinical findings to human.

Accordingly, the present invention provides for a method of differentiating non-human primate (NHP) pluripotent cells, specifically NHP induced pluripotent cells, into NHP hepatocytes. This method comprises the steps of:

a) providing NHP pluripotent stem cells in a feeder-free culture in a chemically defined medium;

b) contacting the pluripotent stem cells with a Wnt signalling activator to produce endodermal cells;

c) contacting the endodermal cells with BMP4 and FGF2 or FGF10 to produce immature NHP hepatocytes; and d) contacting the immature NHP hepatocytes with HGF, OncostatinM and Dexamethasone to produce NHP hepatocytes.

NHP IPSCs can be obtained by reprogramming of somatic cells, e.g. by transduction of defined factors by methods known in the art. Somatic cells transduced with e.g., Oct3/4, Sox2, c-Myc and Klf4 and cultured under ES cell culture conditions acquire properties of ES cells such as morphology, growth rate, potential of unlimited selfrenewal and pluripotency and express ES cell marker genes (see e.g. Takahashi, Yamanaka, Cell. 2006 Aug. 25; 126(4):663-76). Suitable sources of somatic cells are for example, fibroblast cells, keratinocytes or adipocytes obtained by skin biopsy. Other somatic cells suitable as a source for IPSCs are leucocytes cells obtained from blood samples or epithelial cells or other cells obtained from blood or urine samples and reprogrammed to IPSCs by the methods known in the art as described herein. The NHP somatic cells can be obtained from a healthy individual or from a diseased individual. NHP IPSCs have the capacity to develop into cells of the endodermal, ectodermal and mesodermal lineage. In one embodiment provided is a method for differentiating non-human primate (NHP) pluripotent stem cells into NHP hepatocytes, wherein the NHP pluripotent stem cells of step a) are induced pluripotent stem cells (IPSC).

In one embodiment the NHP pluripotent stem cells are derived from a species selected from the group consisting of Cynomolgus monkey (*Macaca fascicularis*) and Rhesus monkey (*Macaca mulatta*). In one preferred embodiment the NHP pluripotent stem cells are derived from Cynomolgus monkey (*Macaca fascicularis*).

In one embodiment the NHP pluripotent stem cells of step a) are provided as single cells and/or in a monolayer of cells. This is opposed to culturing cell clumps or embryoid bodies which constitute less defined formations with various three dimensional structuring. A single cell layer as provided herein is a defined film of cells on an adhesive substrate. In combination with the defined media conditions as described herein a robust and repeatable cell culture system is provided.

In one embodiment the NHP pluripotent stem cells are provided on growth-factor reduced MATRIGEL® (BD Bioscience). MATRIGEL® is a mixture of gelatinous proteins secreted by Engelbreth-Holm-Swarm (EHS) mouse sarcoma cells and is used as a cell culture support to mimic complex extracellular environment as found in many tissues, as e.g., in hepatic tissue. MATRIGEL® is suitable for coating of cell culturing surfaces or embedding cells in "sandwich cultures". Other cell culture support media suitable for culturing cells derived from the hepatic lineage are collagen and laminin.

In one embodiment, the NHP pluripotent cells are provided at a density of about 10000-80000 cells/cm$^2$. In further embodiments, the NHP pluripotent cells are provided at a density of about 20000-70000 cells/cm$^2$ or about 30000-60000 cells/cm$^2$. In one embodiment, the NHP pluripotent cells are provided at a density of about 40000-50000 cells/cm$^2$. In one embodiment the NHP pluripotent stem cells are provided at a density of about 45000 cells/cm$^2$. In one embodiment, IPSCs are provided at a density of about 45000 cells/cm$^2$, i.e. a high density. The inventors of the present method found that providing the cells at a high density increases the efficiency of endodermal and subsequent hepatic differentiation. Optimal initial cell plating density for NHP pluripotent stem cells for maximum hepatocyte yield may be determined for different cell lines.

The cell culturing conditions for differentiating NHP hepatocytes as described herein are chemically defined which means that all individual constituents and their respective concentrations are known. A defined basic medium is supplemented with defined compounds to induce differentiation of the PSCs according to the different steps of the method as described herein. In one embodiment the basic medium is the same for all steps of the method as described herein. In other embodiments, the basic medium is changed after completion of one step of the method and/or after a defined time point. In a preferred embodiment, the basic medium contains Dulbecco's Modified Eagle Medium with Ham's F12 Nutrient Mixture (DMEM/F12) and Gluta-MAX™ supplemented with 1-50 μg/ml insulin, 100-1000 μM monothioglycerole, 0.5-2× Lipid concentrate, 2-20 mg/ml BSA, 10-20 ng/ml sodium selenite, 0.5-2× non-essential amino acids, 1-5 mg/ml heparin, 5-50 μg/ml transferrin, and 100-500 μM ascorbic acid-2-phosphate. In one embodiment the chemically defined medium is MT medium.

The present invention provides a method to produce NHP hepatocytes derived from NHP PSCs in a feeder free cell culture format and in chemically defined media.

In one embodiment, the NHP pluripotent cells are cultivated under conditions permitting stable growth and/or duplication times. For example, the cells are grown in pluripotency medium and passaged several times. In one embodiment, the pluripotency medium is a fully-defined, i.e., serum free, medium comprising a small molecule inhibitor of the Rho-associated coiled-coil forming protein serine/threonine kinase (ROCK) family of protein kinases (herein referred to as ROCK kinase inhibitor).

In one embodiment the ROCK kinase inhibitor is selected from the group of 1-(5-Isoquinolinesulfonyl) homopiperazine), N-Benzyl-2-(pyrimidin-4-ylamino) thiazole-4-carboxamide) and (+)-(R)-trans-4-(1-aminoethyl)-N-(4-pyridyl) cyclo-hexanecarboxamide dihydrochloride). Further ROCK kinase inhibitors useful herein are Fasudil (1-(5-Isoquinolinesulfonyl)homopiperazine), Thiazovivin (N-Benzyl-2-(pyrimidin-4-10 ylamino)thiazole-4-carboxamide) and Y27632 ((+)-(R)-trans-4-(1-aminoethyl)-N-(4-pyridyl) cyclo-hexanecarboxamide dihydrochloride, e.g., Catalogue Number: 1254 from Tocris bioscience). In a preferred embodiment the ROCK kinase inhibitor is Y27632. In one embodiment, the pluripotency medium is a serum free medium comprising 2 to 20 μM Y27632, preferably 5 to 10 μM Y27632. In a preferred embodiment the pluripotency medium is a serum free medium comprising 10 μM Rock kinase inhibitor Y27632. In another embodiment the pluripotency medium is a serum free medium comprising 2 to 20 μM Fasudil. In another embodiment the pluripotency medium is a serum free medium comprising 0.2 to 10 μM Thiazovivin.

NHP PSCs can be expanded infinitely and adapted to large scale cultures suitable for high-throughput screening settings required in drug development and safety testing. Furthermore, NHP PSCs hold great potential for disease modeling and regenerative medicine. NHP PSCs share many physiological similarities with human PSCs and can be used to study neurodegenerative disorders, autoimmune diseases and infection diseases. Importantly, the availability of NHP IPSCs and human IPSCs allows direct comparison of disease or treatment models between NHP and human provided that the IPSCs can be efficiently differentiated into the disease model cell type needed. The methods as disclosed herein can be used to efficiently differentiate NHP PSCs, in particular NHP IPSCs, into NHP hepatocytes.

In one embodiment the NHP PSCs are exposed to ActivinA and FGF-2 prior to differentiation. In one embodiment the NHP pluripotent cells are provided in a chemically defined medium comprising FGF2 and ActivinA. In one embodiment, the defined medium of step a) of the methods comprises 0.3-15 ng/ml ActivinA and 0.3-20 ng/ml FGF-2, preferably 0.3-10 ng/ml ActivinA and 0.3-15 ng/ml FGF-2. In one embodiment the NHP pluripotent cells are provided at a density of about 45000 cells/cm² on growth-factor reduced MATRIGEL®-coated plates in MT basic medium supplemented with 15 ng/ml FGF2, 10 ng/ml ActivinA and 10 μM ROCK kinase inhibitor Y-27632.

In one embodiment the NHP PSCs are washed with a suitable buffer or medium prior to initializing differentiation, to remove any dead cells. Preferably the media are changed in between each step, e.g., the medium is removed, by aspiration or centrifuging the cells and discarding the supernatant and then the medium used in the subsequent step is added to the cells. In one embodiment the cells are washed with a suitable buffer or medium prior to adding the medium of the subsequent step to remove any dead cells and any residual medium or growth factors or cytokines applied in the previous step. Buffers or media useful for washing the cells are known in the art. One example of a suitable buffer for washing the cells is, e.g., phosphate buffered saline (PBS).

To initialize differentiation, the cells are incubated in a defined medium comprising a Wnt pathway activator. In one embodiment, the Wnt pathway activator is compound 21 (3-(3-Amino-phenyl)-4-(1-methyl-1H-indol-3-yl)-pyrrole-2,5-dione, also referred to as "compound 21" or "CP21" herein; see e.g., L. Gong et al; Bioorganic & Medicinal Chemistry Letters 20 (2010), 1693-1696). In several parallel differentiation experiments using different cell densities (30000 to 75000/cm²) and various CP21 concentrations (0 to 2 μM) it was found that using a cell density of 45000/cm² and a CP21 concentration of 1 μM resulted in the most efficient differentiation of pluripotent stem cells into hepatocytes. CP21 concentrations above 2 μM showed decreased cell viability. As prior art protocols require higher concentrations of other modulators of the Wnt pathway (e.g., BIO or CHIR99021) for efficient differentiation this confirms that CP21 is a very potent compound in inducing Wnt signaling.

In one embodiment, the Wnt activator used in step b) of the methods for differentiating NHP pluripotent stem cells into NHP hepatocytes described herein is a compound of formula

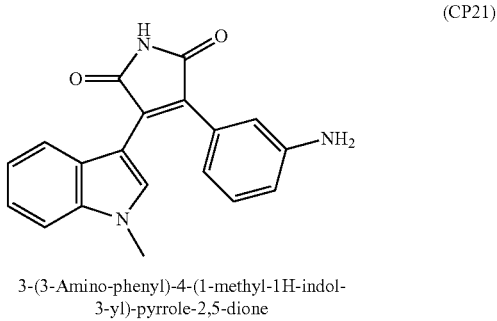 [SMILES: Cn1cc(C2=C(c3cccc(N)c3)C(=O)NC2=O)c2ccccc21]

(CP21)

3-(3-Amino-phenyl)-4-(1-methyl-1H-indol-3-yl)-pyrrole-2,5-dione

In one embodiment, the defined medium of step b) of the differentiation methods comprises 0.1 to 10 μM CP21, preferably 0.5 to 5 μM CP21. In one preferred embodiment step b) the medium comprises 1 μM CP21.

In one embodiment step b) comprises contacting the cells for 12 to 96 hours, preferably for 24 to 72 hours, with a defined medium comprising CP21.

In one preferred embodiment step b) comprises contacting the cells for 72 hours with a defined medium comprising CP21.

The hepatocyte or hepatocyte-like identity can be assessed with expression markers associated with cellular and/or metabolic functions of hepatocytes. The expression markers associated with hepatocyte identity can be expressed at a lower level in hepatocytes derived from PSCs compared to the expression level in primary hepatocytes or liver tissue. The normalized expression level of hepatocyte expression markers in PSC-derived hepatocytes can be 10000× lower, or 1000× lower, or 100× lower, or 10× lower, or 2× lower compared to the expression level of the respective markers in primary hepatocytes or liver tissue. The fold change of expression level of hepatocyte expression markers between PSC-derived hepatocytes and primary hepatocytes can be different for different expression markers. Normalization can be achieved by relating the absolute expression level of a given marker to a suitable house-keeping gene, e.g., GAPDH. Expression markers include but are not limited to hepatocyte specific or hepatocyte characteristic markers related to metabolic functions, protein synthesis, protein storage, transformation of carbohydrates, synthesis of cholesterol, synthesis of bile salts and phospholipids, detoxification, modification and excretion of exogenous and endogenous substances. Typical markers include but are not limited to HNF4a, AFP, ALB, A1AT, SCARB1. Hepatocytes and hepatocyte-like cells are considered to represent cells committed to the same cell lineage expressing similar phenotypic markers. Furthermore, the hepatocyte identity can also be assessed by functional characterization including but not limited to morphology, glycogen and lipid storage.

In one embodiment provided is a method for differentiating non-human primate (NHP) pluripotent stem cells into NHP hepatocytes as described herein, wherein step b) comprises Ly294002. Ly294002 is a PI3K inhibitor and has been shown to support the differentiation of definitive endoderm. In one embodiment, the defined medium of step b) of the method as disclosed herein comprises 0.5 to 100 µM Ly294002, preferably 1 to 20 µM Ly294002. In one preferred embodiment step b) the medium comprises 10 µM Ly294002.

In one embodiment provided is a method for differentiating NHP pluripotent stem cells into NHP hepatocytes as described herein, wherein step b) comprises contacting the cells with Ly294002, and CP21 to induce differentiation.

In one embodiment the medium of step b) comprises 100 ng/ml ActivinA, 10 µM Ly294002 and 1 µM CP21. In one embodiment the cells are incubated with said medium for 3 days, for 2 days, preferentially for 1 day to induce differentiation. Accordingly, provided is a method for differentiating NHP pluripotent stem cells into NHP hepatocytes as described herein, wherein step b) comprises contacting the cells with a chemically defined medium comprising 100 ng/ml ActivinA, 10 µM Ly294002 and 1 µM CP21, in particular for 1 day.

In one embodiment the medium of step b) comprises LDN193189. LDN193189 is an ALK2/3 inhibitor blocking BMP signaling which prevents mesoderm formation. Hepatocytes are from the endodermal lineage, blocking mesoderm formation therefore improves the yield of cells committing to the endodermal lineage. In one aspect of the invention the addition of LDN193189 to the defined medium improves hepatocyte differentiation. In one embodiment, the defined medium of step b) of the methods as described herein comprises 0.1 to 10 µM LDN193189, preferably 0.2 to 2 µM LDN193189. In one preferred embodiment step b) the medium comprises 0.25 µM LDN193189.

In one embodiment step b) comprises contacting the cells for 24 to 96 hours, preferably for 72 hours with a chemically defined medium comprising the Wnt signaling activator CP21. In a further embodiment step b) comprises contacting the cells for about 24 hours with ActivinA, Ly294002 and CP21 followed by contacting the cells for about 48 hours with ActivinA, LDN193189 and CP21. In a particular embodiment, provided is a method for differentiating non-human primate (NHP) pluripotent stem cells into NHP hepatocytes as described herein, wherein step b) comprises contacting the cells with a chemically defined medium comprising 100 ng/ml ActivinA, 0.25 µM LDN193189 and 1 µM CP21 on day 2 and 3 of differentiation.

In one embodiment step b) comprises contacting the cells with a chemically defined medium comprising 50 ng/ml or 100 ng/ml ActivinA on day 4 of differentiation.

In a further embodiment step b) comprises contacting the cells with knock-out serum replacement (KSR). KSR is a defined serum-free formulation comprising amino acids, vitamins, trace elements, transferrin, insulin and lipid-rich albumin and is used as source of nutrients for various cell types. In specific embodiments, the cells are contacted with 0.1 to 10% KSR, with 1 to 5% KSR, preferentially with 2% KSR. In one embodiment step b) comprises contacting the cells for 1 to 6 days, or 3 to 5 days, preferably for 5 days with a chemically defined medium comprising 2% knock-out serum replacement (KSR).

In a further embodiment the cells are contacted with DMSO. In further embodiments, the cells are contacted with 0.1 to 2% DMSO, with 0.2 to 1% DMSO, preferentially with 0.5% DMSO.

In a further embodiment step b) comprises contacting the cells with 2% knock-out serum replacement (KSR) and DMSO. In one embodiment step b) comprises contacting the cells for 24 to 72 hours, preferably for 48 hours with a chemically defined medium comprising 2% knock-out serum replacement (KSR) and 0.5% DMSO.

In a further embodiment step b) comprises contacting the cells for about 24 to 72 hours, preferably for about 48 hours with a chemically defined medium comprising ActivinA, KSR and DMSO. In a particular embodiment, provided is a method for differentiating non-human primate (NHP) pluripotent stem cells into NHP hepatocytes as described herein, wherein step b) comprises contacting the cells with a chemically defined medium comprising 50 ng/ml or 100 ng/ml ActivinA, 2% knock-out serum replacement (KSR) and 0.5% DMSO on day 5 and day 6 of differentiation.

The present invention discloses a method for differentiating non-human primate (NHP) pluripotent stem cells into NHP hepatocytes, wherein the NHP pluripotent stem cells are differentiated in a first step to endodermal cells by contacting the cells with defined factors in defined media as described herein. The endodermal cells can be further differentiated to hepatic endoderm and immature NHP hepatocytes by contacting the cells with defined factors in defined media as described herein.

In one embodiment differentiation of endodermal cells to hepatic endoderm is induced by contacting the cells with bone morphogenetic protein, preferably BMP4 or BMP2 and a fibroblast growth factor, preferably FGF2. BMP4 is involved in bone and cartilage development. In one embodiment combined activation of BMP and FGF signaling is used to differentiate endodermal cells into the hepatic lineage. In one embodiment FGF signaling is induced by a fibroblast growth factor. In one embodiment provided is a method for differentiating NHP pluripotent stem cells into NHP hepatocytes as described herein wherein the fibroblast growth factor of step c) is FGF2 or FGF10. In one embodiment provided is a method for differentiating non-human primate (NHP) pluripotent stem cells into NHP hepatocytes as described herein, wherein step c) comprises contacting the cells with BMP4, and FGF2 or FGF10. In one embodiment step c) comprises contacting the cells for 3 to 5 days, preferably for 4 days with a chemically defined medium comprising BMP4, and FGF2 or FGF10. In specific embodiments, the cells are contacted with about 1 to 50 ng/ml BMP4, with about 2 to 20 ng/ml BMP4, preferentially with 10 ng/ml BMP4. In specific embodiments, the cells are contacted with about 1 to 50 ng/ml FGF2 or FGF10, with about 2 to 20 ng/ml FGF2 or FGF10, preferentially with about 10 ng/ml FGF2 or FGF10. In further embodiments, the cells are contacted with about 0.1 to 2% DMSO, with about 0.2 to 1% DMSO, preferentially with 0.5% DMSO.

In a further embodiment step c) comprises contacting the cells for about 24 to 72 hours, preferably for about 48 hours with KSR, BMP4, FGF2 or FGF10, and DMSO. In a particular embodiment, provided is a method for differentiating NHP pluripotent stem cells into NHP hepatocytes, wherein step c) comprises contacting the cells with a chemically defined medium comprising 2% KSR, 10 ng/ml BMP4, 10 ng/ml FGF2 or FGF10 and 0.5% DMSO on day 7 to day 10 of differentiation.

Accordingly, the present invention discloses a method for differentiating non-human primate (NHP) pluripotent stem cells into NHP hepatocytes, comprising in one step the differentiation of hepatic endoderm cells to immature NHP hepatocytes by contacting the cells with defined factors in defined media as described herein. The immature NHP hepatocytes can be further differentiated to NHP hepatocytes by contacting the cells with defined factors in defined media as described herein.

In one embodiment differentiation of immature NHP hepatocytes to NHP hepatocytes is promoted by contacting the cells with HGF, Oncostatin M and dexamethasone. In one embodiment provided is a method for differentiating NHP pluripotent stem cells into NHP hepatocytes, wherein step d) comprises contacting the cells with HGF, Oncostatin M and dexamethasone. In one embodiment step d) comprises contacting the cells for about 3 to 25 days, for about 4 to 20 days, preferably for 18 days with a chemically defined medium comprising HGF, Oncostatin M and dexamethasone.

In specific embodiments, the cells are contacted with about 1 to 100 ng/ml HGF, with about 5 to 50 ng/ml HGF, preferentially with 20 ng/ml HGF. In further specific embodiments, the cells are contacted with about 1 to 100 ng/ml Oncostatin M, with about 5 to 50 ng/ml Oncostatin M, preferentially with 20 ng/ml Oncostatin M. In further specific embodiments, the cells are contacted with about 5 to 500 ng/ml dexamethasone, with about 20 to 200 ng/ml dexamethasone, preferentially with 100 ng/ml dexamethasone. In further specific embodiments, the cells are contacted with about 0.1 to 2% DMSO, with about 0.2 to 1% DMSO, preferentially with 0.5% DMSO.

In a further embodiment step d) comprises contacting the cells for about 3 to 25 days, for about 5 to 20 days, preferably for 18 days with HGF, Oncostatin M, dexamethasone and DMSO. In a particular embodiment, provided is a method for differentiating NHP pluripotent stem cells into NHP hepatocytes, wherein step d) comprises contacting the cells with a chemically defined medium comprising 20 ng/ml HGF, 20 ng/ml Oncostatin M, 100 nM dexamethasone and 0.5% DMSO from day 11 to day 28 of differentiation.

In one embodiment step d) comprises contacting the cells with a NOTCH signaling inhibitor. Inhibiting NOTCH signaling inhibits the formation of cholangiocytes (bile duct cells). In a particular embodiment, the NOTCH signaling inhibitor is N—[N-(3,5-Difluorophenacetyl)-L-alanyl]-S-phenylglycine t-butyl ester (DAPT). DAPT is a γ-secreatse inhibitor and thus inhibits NOTCH signaling. In one embodiment step d) comprises contacting the cells for about 3 to 7 days, for about 4 to 6 days, preferably for 5 days with a chemically defined medium comprising DAPT. In specific embodiments, the cells are contacted with about 0.1 to 10 µM DAPT, with about 0.2 to 2 µM DAPT, preferentially with 1 µM DAPT. In a particular embodiment, provided is a method for differentiating non-human primate (NHP) pluripotent stem cells into NHP hepatocytes, wherein step d) comprises contacting the cells with a chemically defined medium comprising 1 µM DAPT from day 11 to day 15 of differentiation. In a particular embodiment, provided is a method for differentiating NHP pluripotent stem cells into NHP hepatocytes, wherein step d) comprises contacting the cells with a chemically defined medium comprising 1 µM DAPT from day 11 to day 15 of differentiation.

In one embodiment the medium is changed every day from day 1 to day 15 and thereafter every second day. In a further embodiment the chemically defined medium is changed to a different chemically defined medium at a defined time point e.g., after completion of one of the steps a), b), c) or d) of the provided method for differentiating non-human primate (NHP) pluripotent stem cells into NHP hepatocytes. In one embodiment the chemically defined medium of the steps a), b), c) or d) of the provided method for differentiating non-human primate (NHP) pluripotent stem cells into NHP hepatocytes is MT medium. In one embodiment the chemically defined medium of the steps a), b), c) or d) of the provided method for differentiating non-human primate (NHP) pluripotent stem cells into NHP hepatocytes is MT complete medium. In one embodiment, provided is a method for differentiating non-human primate (NHP) pluripotent stem cells into NHP hepatocytes, wherein step b) and c) comprises changing the chemically defined medium to RPMI1640 supplemented with B27 and non-essential amino acids from day 3 to day 10 of differentiation. In one embodiment, provided is a method for differentiating NHP pluripotent stem cells into NHP hepatocytes, wherein step d) comprises changing the chemically defined medium to HBM medium comprising SingleQuots™ (Lonza) from day 11 to day 28 of differentiation. In one embodiment the chemically defined medium is MT basic medium. In another embodiment the chemically defined medium is changed to RPMI1640 from day 3 to day 10 of differentiation.

Provided herein is a method for differentiating non-human primate (NHP) pluripotent stem cells into NHP hepatocytes. The differentiation state of the NHP hepatocytes can be assessed by testing their capacity to upregulate expression and/or metabolic activity of metabolic enzymes upon treatment with enzyme-inducing drugs. In one embodiment the upregulation of CYP450 enzymes upon treatment with Rifampicin is tested. Uptake and release of rifampicin indicates the presence of hepatocyte specific transporter proteins. Accordingly, in one embodiment the cells are contacted with rifampicin to assess the differentiation state of the cells. In further embodiments the differentiation state of NHP hepatocytes and/or the hepatocyte identity is confirmed by measuring the expression level of metabolic enzymes, in particular CYP450 enzymes. In one embodiment the NHP hepatocytes express CYP450 enzymes as determined by mRNA expression. In one embodiment the expression level of CYP450 enzymes is measured by quantitative real time PCR. In one embodiment the NHP hepatocytes upregulate metabolic enzymes, in particular CYP450 enzymes. In further embodiments the CYP450 enzymes are selected from the group consisting of CYP2B6, CYP3A4, CYP3A7, CYP3A5 and CYP1A2.

The differentiation state of cells obtained by the methods as described herein can also be assessed by measuring cell surface markers specific for hepatocytes. Cell surface markers specific for hepatocytes are known in the art and described herein and can be measured e.g., using flow cytometry or immunocytochemical or immunofluorescent staining of cells. In one embodiment the NHP hepatocytes express at least one hepatic marker selected from AFP, ALB, MAT as determined by immunofluorescent staining.

In one embodiment, the hepatocyte identity is confirmed by the presence of intracellular lipid vesicles, which is indicative of lipid storage. Accordingly, in one embodiment, NHP hepatocytes comprise lipid vesicles. Lipid vesicles can by stained using the Bodipy neutral lipid dye as described herein. In one embodiment, the hepatocyte identity is confirmed using the PAS staining as described herein indicative for glycogen storage in hepatocytes. In one embodiment, NHP hepatocytes exhibiting glycogen storage are provided. In a further embodiment hepatocyte identity is assessed by evaluating the capacity of uptake of indocyanine green which is indicative for the presence of hepatocyte specific transporters as described herein. In one embodiment the NHP hepatocytes take up and release indocyanin green in an in vitro assay.

The innovative method of the present invention provided NHP hepatocytes derived from NHP PSCs, in particular from NHP IPSCs. NHP IPSCs can be generated from cells of healthy or diseased NHP individuals by methods known in the art, wherein the NHP IPSCs are differentiated into NHP hepatocytes using the method described herein. In one embodiment of the present invention provided is a method for generating NHP individual specific hepatocytes.

In one embodiment method for differentiating non-human primate (NHP) pluripotent stem cells into NHP hepatocytes further comprises step e) detaching and f) replating the cells. Previous attempts to replate hepatocytes produced from NHP pluripotent cells in vitro have failed. One of skill in the art can appreciate the advantageous efficiency of being able to replate the NHP hepatocytes, especially for application of these cells in drug screening. The NHP hepatocytes produced by the methods described herein can thereby be used in cultures of various formats and assays of various scale as described herein, which is important for research, development and commercial uses.

Accordingly, provided herein is a method of preparing an in vitro NHP hepatocyte assay, the method comprising the steps of:
 i) providing NHP hepatocytes prepared by the method as described herein;
 ii) contacting the NHP hepatocytes for between about 1 and about 3 hours with Accutase to detach the NHP hepatocytes;
 iii) replating the detached NHP hepatocytes in a suitable assay format.

Replating can be used to further increase the purity of the NHP hepatocytes, especially if used in conjunction with cell sorting as described herein. In one embodiment said method further comprises sorting of NHP hepatocytes. Prior to sorting the cells are enzymatically dissociated as described herein. Methods of cell sorting based on phenotypic markers such as cell size, enzymatic activity or cell surface expression of one or more marker, or a combination thereof, are well known in the art and can be used in combination with the methods described herein to enrich for cells expressing a defined marker on the cell surface, in particular for cells expressing a hepatocyte marker on the cell surface. Accordingly provided herein is a method of preparing an in vitro NHP hepatocyte assay, wherein the detached NHP hepatocytes are enriched for cells expressing a hepatocyte marker on the cell surface.

Examples of cell sorting methods include flow cytometry including fluorescence activated cell sorting (FACS) and magnetic activated cell sorting (MACS). In a preferred embodiment, NHP hepatocytes expressing the cell surface marker SCARB1 are enriched. In another preferred embodiment the hepatocyte marker used in the replating step as disclosed herein is SCARB1. The methods described herein for the first time identify SCARB1 as suitable marker for enriching NHP hepatocytes. Flow cytometry analysis presented herein demonstrated that SCARB1 positive cells in a culture can be enriched from less than 40% to up to 60% or more of the total cells, specifically, from less than 20% to up to 80% or more of the total cells. The majority of cells in the SCARB1 positive fraction show typical hepatocyte morphology. Gene expression analysis of sorted and unsorted cells reveal higher expression levels of hepatocyte-specific genes in SCARB1 positive compared to SCARB1 negative cells confirming the usefulness of SCARB1 as a marker for enrichment of hepatocytes.

Accordingly provided is a method for purifying hepatocytes using magnetic associated cell sorting (MACS) of cells expressing the surface marker SCARB1. This method enriches hepatocytes, e.g., for replating into culture vessel formats suitable for screening applications, e.g., high-throughput candidate drug compound screening. For this purpose, coating matrices enabling long-term culture of hepatocytes e.g., to assess chronic drug toxicity are provided herein. The enriched NHP hepatocytes obtained by the method as described herein can be replated onto laminin, collagen or preferably on matrigel. In one embodiment the NHP hepatocytes are replated in as a matrigel sandwich culture as described herein.

In a particular embodiment of the present invention provided is a method for differentiating NHP pluripotent stem cells into NHP hepatocytes, the method comprising the steps of:
 a) providing NHP pluripotent stem cells in a feeder-free culture in a chemically defined medium;
 b) contacting the pluripotent stem cells with a Wnt signalling activator to produce endodermal cells;
 c) contacting the endodermal cells with BMP4 and FGF2 or FGF10 to produce immature NHP hepatocytes; and
 d) contacting the immature NHP hepatocytes with HGF, OncostatinM and Dexamethasone to produce NHP hepatocytes;
 e) contacting the NHP hepatocytes for between about 1 and about 3 hours with Accutase to detach the NHP hepatocytes, wherein the detached NHP hepatocytes are enriched for SCARBI-positive cells; and
 f) replating the detached NHP hepatocytes in a suitable assay format.

Importantly, the method of the present invention provides NHP hepatocytes with an increased yield of cells with hepatocyte identity as described herein. Hepatocyte identity can be assessed using methods as described herein. The innovative methods presented herein are suitable to differentiate NHP pluripotent stem cells, such as NHP IPSCs, into hepatocytes with a yield of more than 10%, more than 20%, more than 30%, more than 40%, more than 50%, more than 60%, more than 70%, preferably more than 80% of total cells. In one embodiment, NHP-IPSC-derived hepatocytes produced by the methods described herein are provided with a yield of more than 10% SCARBI-positive cells, more than 20% SCARBI-positive cells, more than 30% SCARBI-positive cells, more than 40% SCARBI-positive cells, more than 50% SCARBI-positive cells, more than 60% SCARBI-positive cells, more than 70% SCARBI-positive cells, preferably more than 80% SCARBI-positive cells of total cells in culture. These NHP-IPSC-derived hepatocytes display characteristic hepatocyte morphology as well as gene and protein expression of hepatocyte-specific markers, in particular CYP enzymes. On the functional level, provided are cells that show storage of lipids and glycogen, transporter activity and drug-induced upregulation of CYP enzyme expression.

In one embodiment provided is a feeder-free NHP hepatocyte culture in a chemically defined medium. In one embodiment provided is a NHP hepatocyte obtained by a method as described herein. NHP hepatocytes derived from healthy or diseased individuals represent a predictive in vitro model to study the pathophysiology of diseases like e.g., fatty liver and liver cirrhosis and/or for primate specific pathogens like e.g., Hepatitis viruses.

The media used in the presented methods is fully defined. The absence of undefined components is important to ensure reproducibility and robustness of the method as described herein. Accordingly, the NHP hepatocytes derived from the method of the present invention are well suitable for compound screening and disease modeling.

In a further aspect, the generation of a BioBank of NHP hepatocytes is envisaged. In one embodiment provided is a biobank of NHP hepatocytes obtained by a method as described herein. In one embodiment, a BioBank comprising different populations of hepatocytes obtained from different NHP individuals is generated. The NHP individuals may be healthy or diseased. In one aspect, a BioBank of NHP hepatocytes derived from different NHP individuals is used to model genetic variation among NHP populations, particularly regarding drug metabolism. The term "BioBank" as used herein means a library of biological samples taken from different individuals or species. The hepatocytes obtained by the method as described herein can be cryopreserved in storing them in liquid nitrogen in the presence of a cryoprotective agent such as DMSO. The archived collection of specimen and associated data is intended for research purposes with the aim of studying the pathophysiology of diseases or for drug discovery and toxicity screening as described herein.

NHP-PSC-derived hepatocytes present a physiologically relevant in vitro liver system for various applications in research and development, e.g., drug discovery and screening. Said in vitro liver system is scalable and therefore suitable for high-throughput screening without the need to sacrifice animals. Furthermore, the provided method is robust and reproducible since the same lineages or even one clone of PSCs can be used to produce any suitable number of hepatocytes. PSCs can be readily frozen and stored over long periods of time also accounting for the reproducibility of the system.

In a further embodiment, the NHP PSC-derived hepatocytes described herein for use in drug development is provided. In one embodiment, use of the NHP PSC-derived hepatocytes for assessing drug toxicity is provided. The NHP hepatocytes provided according to the method as described herein can be contacted with a compound to be tested for hepatotoxicity and the NHP hepatocytes assesses for viability after a defined incubation time with the test compound. In one embodiment provided is a method for testing the potential toxicity of a compound, the method comprising the steps of: (i) exposing one or more NHP hepatocytes prepared according to the method as described herein to the compound; and (ii) monitoring the one or more mature NHP hepatocytes for signs of toxicity. In a further embodiment provided is a method for testing the potential toxicity of a compound, the method comprising the steps of: (i) exposing one or more hepatocytes prepared according to the method as described herein to the compound, whereby the compound is metabolized by the hepatocytes; (ii) contacting the resulting metabolite of the compound with one or more non-hepatocyte cells; and (iii) monitoring the one or more non-hepatocyte cells for any metabolite-induced changes.

In yet a further embodiment the NHP PSC-derived hepatocytes described herein are used as a model to evaluate toxicity, off targets and/or efficacy of therapeutic modalities based on antisense therapy (e.g., LNAs). For therapies or therapy strategies related or targeted to specific DNA sequences NHPs are often the only relevant species because of the high sequence homology to human (about 98%). Accordingly, provided is a method to evaluate toxicity, off targets and/or efficacy of LNAs for use in human therapy, wherein the NHP sequence targeted by a specific LNA has a sequence homology to the respective human sequence of at least 95%, at least 96%, at least 97% at least 98% or at least 99%.

In one embodiment, use of the NHP PSC-derived hepatocytes for in vitro infection model is provided. NHP hepatocytes produced with the methods described herein can be infected with pathogens with a high host specificity for primates (human and non-human primates) or with NHP specific pathogens that can be used as surrogate model for related human-specific pathogens. In a specific embodiment NHP hepatocytes are infected with a virus selected from the group consisting of Hepatitis A virus, Hepatitis B virus, Hepatitis C virus, particularly as in vitro model for liver infection.

In one embodiment provided is the use of the NHP hepatocytes obtained by a method as described herein or of the biobank as described herein as in vitro model for diseases caused by dysfunction of liver cells. In a further embodiment provided is the use of the NHP hepatocytes obtained by a method as described herein or of the biobank as described herein as in vitro model for infection of liver cells. In one embodiment the infection is selected from the group consisting of viral infection, bacterial infection, fungal infection, or parasitic infection. In a particular embodiment the viral infection is selected from the group consisting of Hepatitis A virus infection, Hepatitis B virus infection, Hepatitis C virus infection. In a preferred embodiment the viral infection is a Hepatitis B virus infection.

In a further embodiment the hepatocytes obtained by this method can be used as a host system to model viral life cycle, e.g. viral entry, viral replication and viral release. Provided is an in vitro method for supporting the life cycle of a virus, the method comprising the step of exposing one or more NHP hepatocytes prepared according to the method as described herein to the virus, wherein the virus replicates within the one or more NHP hepatocytes. Accordingly, the cells of the present invention can be used as in vitro infection model of a virus.

In another embodiment the hepatocytes obtained by this method are used for screening and evaluating new targets and compounds for treatment of liver diseases, e.g., those mentioned herein. In one embodiment, the hepatocytes obtained by the methods described herein are derived from diseased subjects. Differentiating hepatocytes from diseased subjects represents a unique opportunity to early evaluate drug safety in a non-human primate background paradigm.

In another embodiment the hepatocytes obtained by this method are used as an in vitro model of the liver. In another embodiment the hepatocytes obtained by this method are used to model a human disease by introducing one or several mutations associated with a diseased state in humans or by using and PSC lineage comprising the one or more human disease-related mutations and differentiating the PSCs to NHP hepatocytes as described herein.

In another embodiment the hepatocytes obtained by this method are used to prepare an in vitro NHP hepatocyte assay. Said in vitro NHP hepatocyte assay is scalable and therefore suitable for high-throughput screening without the need to sacrifice animals. Furthermore, the provided method is robust and reproducible as the same PSCs can be reused or frozen aliquots of defined PSCs can be used consecutively to ensure assay homology. Importantly, data generated with the IPSC-derived hepatocytes obtained by the methods as described herein can be directly compared to results generated with human IPSC-derived hepatocytes as described herein. In one embodiment provided is a method for direct inter-species comparison in the same in vitro assay system and subsequent analysis of species-specific responses.

Any of the above embodiments may be used singly or in combination.

EXEMPLARY EMBODIMENTS

1. A method for differentiating non-human primate (NHP) pluripotent stem cells into NHP hepatocytes, the method comprising the steps of:
   a) providing NHP pluripotent stem cells in a feeder-free culture in a chemically defined medium;
   b) contacting the pluripotent stem cells with a Wnt signalling activator to produce endodermal cells;
   c) contacting the endodermal cells with BMP4 and a fibroblast growth factor to produce immature NHP hepatocytes; and
   d) contacting the immature NHP hepatocytes with HGF, OncostatinM and Dexamethasone to produce NHP hepatocytes.
2. The method of embodiment 1, wherein the chemically defined medium is MT medium.
3. The method of any one of embodiments 1 and 2, wherein the NHP pluripotent stem cells are provided in a chemically defined medium comprising FGF2 and ActivinA.
4. The method of any one of embodiments 1 to 3, wherein the NHP pluripotent stem cells are provided on growth-factor reduced MATRIGEL®.
5. The method of any one of embodiments 1 to 4, wherein the NHP pluripotent stem cells are provided at a density of about 45000 cells/cm².
6. The method of any one of embodiments 1 to 5, wherein the NHP pluripotent cells are provided at a density of 45000 cells/cm² on growth-factor reduced MATRIGEL®-coated plates in MT basic medium supplemented with 15 ng/ml FGF2, 10 ng/ml ActivinA and 10 µM ROCK kinase inhibitor Y-27632.
7. The method of any one of embodiments 1 to 6, wherein the medium is changed every day from day 1 to day 16 and thereafter every second day.
8. The method of any one of embodiments 1 to 7, wherein step b) and c) comprise contacting the cells with RPMI1640 comprising B27 and NEAA from day 3 to day 10 of differentiation.
9. The method of any one of embodiments 1 to 8, wherein the Wnt signalling activator is CP21
10. The method of any one of embodiments 1 to 9, wherein step b) comprises contacting the cells with Ly294002 and CP21 to induce differentiation.
11. The method of any one of embodiments 1 to 10, wherein step b) comprises contacting the cells with a chemically defined medium comprising 100 ng/ml ActivinA, 10 µM Ly294002 and 1 µM CP21 on day 1.
12. The method of any one of embodiments 1 to 11, wherein step b) comprises contacting the cells with LDN193189.
13. The method of any one of embodiments 1 to 12, wherein step b) comprises contacting the cells with a chemically defined medium comprising 100 ng/ml ActivinA, 0.25 µM LDN193189 and 1 µM CP21 on day 2 and day 3 of differentiation.
14. The method of any one of embodiments 1 to 13, wherein step b) comprises contacting the cells with a chemically defined medium comprising 50 ng/ml or 100 ng/ml ActivinA on day 4 of differentiation.
15. The method of any one of embodiments 1 to 14, wherein step b) comprises contacting the cells with knock-out serum replacement (KSR) and DMSO.
16. The method of any one of embodiments 1 to 15, wherein step b) comprises contacting the cells with a chemically defined medium comprising 50 ng/ml or 100 ng/ml ActivinA, 2% knock-out serum replacement (KSR) and 0.5% DMSO from day 5 and day 6 of differentiation.
17. The method of any one of embodiments 1 to 16, wherein the fibroblast growth factor of step c) is FGF2 or FGF10.
18. The method of any one of embodiments 1 to 17, wherein step c) comprises contacting the cells with BMP4, DMSO and FGF2 or FGF10.
19. The method of any one of embodiments 1 to 18, wherein step c) comprises contacting the cells with a chemically defined medium comprising 2% KSR, 10 ng/ml BMP4, 10 ng/ml FGF2 or FGF10, and 0.5% DMSO from day 7 to day 10 of differentiation.
20. The method of any one of embodiments 1 to 19, wherein step d) comprises contacting the cells with a chemically defined medium comprising 20 ng/ml HGF, 20 ng/ml Oncostatin M, 100 nM dexamethasone and 0.5% DMSO from day 11 to day 28 of differentiation.
21. The method of any one of embodiments 1 to 20, wherein step d) comprises contacting the cells with a NOTCH signaling inhibitor.
22. The method of any one of embodiments 1 to 21, wherein step d) comprises contacting the cells with a chemically defined medium comprising 1 µM DAPT from day 11 to day 15 of differentiation.
23. The method of any one of embodiments 1 to 22, wherein step d) comprises changing the chemically defined medium to HBM medium comprising SingleQuots™ (Lonza) from day 11 to day 28 of differentiation.
24. The method of any one of embodiments 1 to 23, wherein the cells take up and release rifampicin indicating the presence of hepatocyte specific transporter proteins.
25. The method of embodiments 1 to 24, wherein the NHP hepatocytes upregulate metabolic enzymes.
26. The method of any one of embodiments 1 to 25, wherein the NHP hepatocytes comprise lipid vesicles.
27. The method of any one of embodiments 1 to 26, wherein the NHP hepatocytes express at least one hepatic marker selected from the group consisting of AFP, ALB and αIAT.
28. The method of any one of embodiments 1 to 27, wherein the NHP hepatocytes take up and release indocyanin green in an in vitro assay.

29. The method of any one of embodiments 1 to 28, wherein the NHP hepatocytes express CYP450 enzymes.
30. The method of any one of embodiments 1 to 29, wherein the NHP pluripotent stem cells of step a) are induced pluripotent stem cells (IPSCs).
31. The method of any one of embodiments 1 to 30 wherein the NHP pluripotent stem cells are derived from a species selected from the group consisting of Cynomolgus monkey (Macaca fascicularis) and Rhesus monkey (Macaca mulatta).
32. A feeder-free NHP hepatocyte culture in a chemically defined medium.
33. A NHP hepatocyte obtained by a method according to any one of embodiments 1 to 31.
34. A biobank of NHP hepatocytes obtained by a method according to any one of embodiments 1 to 31.
35. Use of the NHP hepatocytes obtained by a method according to any one of embodiments 1 to 31 or of the biobank of embodiment 34 as in vitro model for diseases caused by dysfunction of liver cells.
36. Use of the NHP hepatocytes obtained by a method according to any one of embodiments 1 to 31 or of the biobank of embodiment 34 as in vitro model for infection of liver cells.
37. The use of embodiment 36, wherein infection is selected from the group consisting of viral infection, bacterial infection, fungal infection, or parasitic infection.
38. The use of embodiment 37, wherein the viral infection is selected from the group consisting of Hepatitis A virus infection, Hepatitis B virus infection, Hepatitis C virus infection, Eppstein Barr virus infection.
39. The use of embodiment 38, wherein the viral infection is a Hepatitis B virus infection.
40. A method for testing the potential toxicity of a compound, the method comprising the steps of: (i) exposing one or more NHP hepatocytes prepared according to the method of any one of embodiments 1 to 31 to the compound; and (ii) monitoring the one or more mature NHP hepatocytes for signs of toxicity.
41. A method for testing the potential toxicity of a compound, the method comprising the steps of: (i) exposing one or more NHP hepatocytes prepared according to the method of any one of embodiments 1 to 31 to the compound, whereby the compound is metabolized by the NHP hepatocytes; (ii) contacting the resulting metabolite of the compound with one or more non-hepatocyte cells; and (iii) monitoring the one or more non-hepatocyte cells for any metabolite-induced changes.
42. An in vitro method for supporting the life cycle of a virus, the method comprising the step of exposing one or more NHP hepatocytes prepared according to the method of any one of embodiments 1 to 31 to the virus, wherein the virus replicates within the one or more NHP hepatocytes.
43. Use of any of the cells of any one of the embodiments 1 to 31 for in vitro testing of toxicity of a compound.
44. Use of any of the cells of any one of the embodiments 1 to 31 as in vitro infection model of a virus.
45. A method of preparing an in vitro NHP assay, the method comprising the steps of:
   i) providing NHP hepatocytes prepared by the method of any one of embodiments 1 to 31;
   ii) contacting the NHP hepatocytes for between about 1 and about 3 hours with Accutase to detach the NHP hepatocytes;
   iii) replating the detached NHP hepatocytes in a suitable assay format.
46. The method of embodiment 45, wherein the detached NHP hepatocytes are enriched for SCARBI-positive cells before replating.
47. The method of embodiment 46, wherein the cells are enriched using fluorescence activated or magnetic-activated cell sorting.
48. The method of any one of embodiments 45 to 47, wherein the NHP hepatocytes are replated onto laminin, collagen or matrigel.
49. The method of any one of embodiments 45 to 47, wherein the NHP hepatocytes are replated as a matrigel sandwich culture.
50. The methods and used essentially as described herein.

EXAMPLES

The following are non-limiting examples of compositions and methods of the invention. It is understood that various other embodiments may be practiced, given the general description provided above.

General Methods

Cell Culture

Cynomolgus fibroblast-derived IPSCs were cultured on MATRIGEL® (BD Bioscience)-coated plates in MT basic medium (DMEM/F12+Glutamax with insulin 7 µg/ml, monothioglycerole 450 µM, 1× Lipid concentrate (Thermo Fisher), BSA 5 mg/ml, sodium selenite 14 ng/ml, 1× non-essential amino acids, heparin 2 mg/ml, transferrin 15 µg/ml, 220 µM ascorbic acid-2-phosphate) with the addition of bFGF 15 ng/ml and ActivinA 10 ng/ml (MT complete medium) at 37° C. and 5% $CO_2$. Cells were passaged every 2-4 days incubating using Gentle Cell Dissociation Reagent (GCD).

Detachment of cells for passaging was performed either with Accutase (StemCell Technologies) for 1 to 3 minutes at 37° C. or Gentle Cell Dissociation (GCD, StemCell Technologies) for 7 minutes at RT, dependent whether single cells or cells in colonies were needed.

For dissociation with Accutase, cells were washed with PBS, Accutase was added for 1 to 3 minutes at 37° C. and inactivated with the same volume of MT basic medium and cells were collected. After centrifugation for 5 minutes at 200 g, cells were resuspended in MT complete medium with 10 µM Rock-inhibitor Y-27632 and seeded.

For detachment with GCD, cells were washed with PBS, GCD was added for 7 minutes at RT and removed afterwards. Cells were carefully resuspended in MT complete medium and seeded.

Hepatocyte Differentiation of Cynomolgus IPSCs

Cynomolgus IPSCs were seeded at d0 in a density of 45000 cells/cm$^2$ on growth-factor reduced MATRIGEL® (BD Bioscience)-coated plates in MT basic medium+15 ng/ml FGF2, 10 ng/ml ActivinA and 10 µM Rock-Inhibitor Y-27632. Generally, media change was performed every day until day 16 and afterwards every second day. Basic medium for differentiation was MT basic medium (DMEM/F12+Glutamax with insulin 7 µg/ml, monothioglycerole 450 µM, 1× Lipid concentrate, BSA 5 mg/ml, sodium selenite 14 ng/ml, 1× non-essential amino acids, heparin 2 mg/ml, transferrin 15 µg/ml, 220 µM ascorbic acid-2-phosphate) or changing to RPMI1640 medium+B27 1:50+non-essential amino acids 1:100 from day 3 of differentiation onwards. On day 1 of differentiation, medium was changed to MT basic medium with 100 ng/ml ActivinA, 10 μM Ly294002 and 1 μM CP21 (Roche GSK3β inhibitor). Then, cells were treated for two days with 100 ng/ml ActivinA, 0.25 μM LDN193189 and 1 μM CP21. At day 4, the medium was changed for three days to the supplements 50 ng/ml ActivinA, 2% knock-out serum replacement (KSR) and 0.5% DMSO. The protocol was modified to a prolonged step of high ActivinA which consisted of 100 ng/ml ActivinA at day 4 of differentiation. To induce hepatic specification, cells were maintained for four days in medium supplemented with 2% KSR, 10 ng/ml BMP4, 10 ng/ml FGF2 or FGF10 and 0.5% DMSO. From day 11 onwards, hepatocyte-like cells were cultured in hepatocyte maturation medium consisting of MT medium supplemented with 20 ng/ml HGF, 20 ng/ml Oncostatin M, 100 nM dexamethasone and 0.5% DMSO. Modification included the addition of 1 μM DAPT between day 11 and day 20. Further modifications included the change of the basis medium for maturation at day 11 to HBM medium+SingleQuots™ (Lonza).

Immunofluorescence Staining and Flow Cytometry Analysis

Cells were fixed with 4% PFA and then permeabilized with 0.1% TritonX in PBS (including Ca2+ and Mg2+). After blocking with 0.1% TritonX in SuperBlock, cells were stained with primary antibodies for 1 to 2 hours at RT or overnight at 4° C. The used antibodies are depicted in Table 2. Subsequently, cells were washed and stained with secondary antibodies conjugated to Alexa488 (1:1000), Alexa555 (1:1000), and Alexa647 (1:200) (all from molecular probes) for 1 to 2 hours at RT or overnight at 4° C. Nuclei were stained with Hoechst 1:1000 (Molecular Probes) for 5 minutes. Between incubations, samples were washed with PBS (including Ca2+ and Mg2+). Cells were imaged using a Zeiss inverted microscope. Images were analyzed using ImageJ software. Quantifications of staining was performed using an Operetta imaging system and the Harmony image analysis software (PerkinElmer).

TABLE 2

List of primary antibodies and their dilution used for immunofluorescence staining.

| antigen | supplier | species | catalog number | dilution |
| --- | --- | --- | --- | --- |
| OCT3/4 | SantaCruz | goat | sc-8629 | 1:200 |
| SOX2 | millpore | rabbit | AB5603 | 1:500 |
| SOX1 | SantaCruz | goat | sc-17318 | 1:250 |
| NANOG | SantaCruz | rabbit | sc-33759 | 1:100 |
| FOXA2 | abcam | rabbit | ab40874 | 1:500 |
| SOX17 | R&D Systems | goat | AF1924 | 1:500 |
| AFP | sigma | mouse | A8452 | 1:250 |
| α1AT | Dako | rabbit | A0012 | 1:2000/1:5000 |
| ALB | Cedarlane | mouse | CL2513A | 1:500 |

For flow cytometry, cells were detached with Accutase and stained for 15 minutes at 4° C., dark in 100 μl MACS running buffer (Miltenyi biotec) containing primary antibodies (Table 3): 5 μl anti-CXCR4, 5 μl anti-Thrombomodulin, 10 μl anti-KDR, or 2.5 μl anti-CD238 per 0.5×10⁶ cells, for more than 0.5×10⁶ cells the double amount of antibody was used. Afterwards, cells were washed with MACS running buffer, and resuspended in 500 μl MACS running buffer. Flow cytometry was performed using a BD FACS Canto, and data were analyzed with FlowJo software.

TABLE 3

Antibodies used for flow cytometry analysis and MACS sorting.

| antigen | conjugate | supplier | catalog number |
| --- | --- | --- | --- |
| SCARB1 | PE | Biolegend | 363204 |
| ASGR1 | PE | | |
| CD184/CXCR4 | APC | Biolegend | 306510 |
| CD309/KDR | PE | Miltenyi Biotec | 130-093-598 |

Replating

At day 21 of differentiation, immature hepatocytes were dissociated with different reagents for the time indicated in FIG. 9A and seeded in MT basic medium supplemented with 20 ng/ml HGF, 20 ng/ml Oncostatin M, 100 nM dexamethasone and 0.5% DMSO on collagen-coated wells (10 μg/cm²), which were washed 1× with PBS before plating. The different dissociation conditions were EDTA/PBS for 3 hours, GCD for 3 hours, Collagenase overnight, Dispase for 3 hours and trypsin 0.25% for 1 hour, Accutase for 3 hours, Accutase overnight, trypsin 0.05% for 3 hours and trypsin 0.25% for 1 h. Dissociation with Accutase was inactivated with MT basic medium, trypsin was inhibited with trypsin inhibitor 1:1. The next day, clumps of non-attached cells were transferred to 125 μl cold hepatocyte maturation medium+125 μl undiluted growth-factor reduced MATRIGEL® (GFR-MG, BD Bioscience), after 4 hours 100 μl medium was added in order to embed the clumps in MATRIGEL®.

At day 22 of differentiation, detachment with each dissociation reagent was performed with each one well differentiated with DAPT (Calbiochem) or without the addition of DAPT. GFR-MG 1:40 was added to the medium just before plating on collagen-coated wells. Each 1 well was detached with trypsin 0.25% for 15 minutes, resuspended after addition of 500 μl PBS (without $Ca^{2+}$ and $Mg^{2+}$), centrifuged and replated. The same procedure was performed with Accutase for 1 hour. Each 1 well was detached with Accutase for 1 hour, resuspended after addition of 500 μl PBS (without $Ca^{2+}$ and $Mg^{2+}$), centrifuged and replated on uncoated 24-well plates. Cells were allowed to attach for 1 hour, the supernatant was taken and cells plated on collagen-coated wells with addition of GFR-MG. Cells in uncoated wells were cultivated as well.

For all previously mentioned replating experiments, cells were transferred at a ratio 2:1 regarding growth area of the cell culture dishes (e.g., hepatocytes from 2×6 wells were transferred to 1 6 well). Every other day, 50% of medium was exchanged with hepatocyte maturation medium.

The following differentiation was performed in B6 plates. Cells were dissociated with one of the following conditions: Accutase for 1 hour, trypsin 0.25% for 15 minutes, or manual isolation of hepatocyte colonies. Cells were transferred at a ratio 2:1 as described above. For the first media change, GFR-MG was added 1:40 to the medium. Medium change was performed every day.

Magnetic-Activated Cell Sorting

Magnetic-activated cell sorting (MACS) of SCARB1-positive cells was performed at day 22 or day 29 of hepatocyte differentiation. Cells were detached with Accutase, filtered through a 100 μm cell strainer, centrifuged and resuspended in cold MACS running buffer for counting. After centrifugation at 200 rpm for 5 minutes, cells were resuspended in 95 µl buffer supplemented with 5 µl anti-SCARB1-PE antibody per 1×10⁶ cells and incubated for 15 minutes, dark, at 4° C. Cells were washed by addition of 10× volume of MACS running buffer and centrifuged. The cells were resuspended in 80 µl cold MACS running buffer and 20 µl anti-PE microbeads (Miltenyi Biotec) per 1×10⁷ cells and incubated for 15 minutes, dark. Cells were washed by addition of 10× volume MACS running buffer, centrifuged, resuspended in 500 µl buffer, filtered through a 70 µm cell strainer and subjected to MACS using an autoMACSpro separator (Miltenyi). All fractions were counted, 1×10⁵ cells per sample subjected to flow cytometry analysis and the SCARB1+cells were seeded on plates in differentiation medium of day 22/29 at a density of 100'000 to 200'000 cells/cm². The following coating procedures were used: Laminin 521 (20 µg/ml), Collagen (10 µg/cm2), and growth factor reduced MATRIGEL® (1:20 dilution). Plates were centrifuged for 3 minutes at 300 rpm to enhance attachment of cells. MATRIGEL® sandwich coating was performed 24 hours after seeding. Medium was removed from the cells and replaced by cold hepatocyte maturation medium containing GFR-MG at a dilution of 1:20. Cells were incubated at 37° C., 5% $CO_2$ for 1 hour, then 2× volume of prewarmed hepatocyte maturation medium was added Staining of Differentiated Hepatocytes BODIPY Staining Staining of lipid droplets in differentiated hepatocytes was performed with Bodipy neutral lipid dye (Invitrogen, D3922). The Bodipy solution was diluted 1:1000 in medium and incubated for 20 minutes on the cells at 37° C. Cells were washed 1× with PBS and Bodipy fluorescence was analyzed using a fluorescence microscope.

PAS Staining

Cells on day 28-30 of differentiation were fixed with 4% paraformaldehyde in water for 10 minutes and washed 1× with double distilled water. Afterwards, the cells were stained with PAS staining kit (Sigma-Aldrich): 5 minutes with 1% periodic acid solution, washed 5 times with double distilled water, 15 minutes incubation with Schiff's solution and washed with tap water for 5 times.

Indocyanine Green Uptake

The indocyanine green powder (ICG, Sigma) was freshly dissolved in DMSO at 100 mg/ml, then added to the culture medium of differentiated hepatocytes to a final concentration of 1 mg/ml. After incubation at 37° C. for 60 minutes, the medium with ICG was discarded, the cells were washed 3 times with PBS and new culture medium was added. The cellular uptake of ICG was examined by microscopy. To monitor the release of the ICG, the wells were cultured for an additional 24 hours.

Gene Expression Analysis of CYP-P450 Enzymes

Primary cynomolgus hepatocytes were cultured in Williams E Medium supplemented with 5% FBS, 0.5% Penicillin/Streptomycin, human recombinant insulin 6.25 µg/ml, human transferrin 6.25 µg/ml, selenous acid 6.25 µg/ml, BSA 1.25 mg/ml, linoleic acid 5.35 µg/ml, GlutaMAX 2 mM, HEPES pH 7.4 15 mM, 0.1 µM dexamethasone in DMSO, the day before assay performance. Primary hepatocytes and hepatocytes derived from cynomolgus IPSCs were treated with DMSO, Rifampicin, dexamethasone and subjected to CYP assay and RNA isolation for qRT-PCR.

CYP-P450—Glo Assay

To determine the CYP-P450 activity cells derived from cynomolgous IPSCs, the cells of the hepatocyte differentiation as well as primary cynomolgous hepatocytes as positive control were cultured in 24-well plates. Cells were treated with DMSO 1:200, 25 µM Rifampicin or 50 µM dexamethasone in culture medium (MT basic without supplements) for 24 hours. Subsequently, the CYP activity was measured with the P450 Glo assay Kit (Promega) for CYP3A4 activity according to the manufacturer's instructions and the luminescence was measured. The cell treatment was performed in duplicates and the second plate was subjected to RNA isolation.

Gene Expression Analysis

Cells were lysed in 350 µl RLT lysis buffer (Qiagen) supplemented with β-Mercaptoethanol 1:100 per 1 well of a 24-well plate and RNA was isolated with RNeasy Mini Kit (Qiagen) according to the manufacturer's instructions including the optional DNAse digest step and elution with 30 µl water. Transcription to cDNA was performed with Transcriptor first strand DNA synthesis Kit (Roche) according to the manufacturer's instructions for Procedure B including the optional denaturation step.

Primers (forward and reverse) and probes (UPL) for qRT-PCR are depicted in Table 4. The UPL probes are commercially available probes from Roche Diagnostics (lifescience.roche.com).

The qPCR was performed in 384-well plates with 10 µl reaction volume. Each 5.6 ng cDNA or control RNA was used per sample in combination with each 0.4 µM forward and reverse primer, 0.2 µM UPL probe and 1× LightCycler 480 Probes Master. The experiment was performed in technical triplicates. The Roche LightCycler-480 system was run with the program shown in Table 5.

TABLE 4

Taqman primers and probes used for gene expression analysis of CYP-P450 enzymes.

| Gene | primer forward/reverse | UPL probe |
| --- | --- | --- |
| GAPDH | gaaggtgaaggtcggagtca<br>aaccatgtagttgaggtcaatgaa | UPL 147 |
| CYP2B6 | gaagcttttatccccttctcct<br>gggtgtcagatcgatgtcttc | UPL 35 |
| CYP3A4 | tgtgttggtgagaaatctgagg<br>ctgtaggccccaaagaca | UPL 38 |
| CYP3A7 | gtgctggtgagaaatctgagg<br>ctgtaggccccaaagacg | UPL 38 |
| CYP3A5 | ggagttccgccctgaaag<br>tccagttccaaagggtgtgt | UPL 56 |
| CYP1A2 | taatatcaagcacttgcctctaca<br>ccctgagcacccagaatacc | UPL 53 |
| ALB | gatgtcttcctgggcatgtt<br>tggcttcgtatgccttgg | UPL 146 |

TABLE 5

LightCycler program for qRT-PCR analysis.

| Program | Cycles | Analysis | Temperature | Acq. Mode | Time | Ramp ° C./s |
| --- | --- | --- | --- | --- | --- | --- |
| Pre-Incubation | 1 | None | 95° C. | None | 10 min | 4.8 |
| Amplification | 50 | Quanti- | 95° C. | None | 10 sec | 4.8 |

TABLE 5-continued

LightCycler program for qRT-PCR analysis.

| Program | Cycles | Analysis | Temperature | Acq. Mode | Time | Ramp ° C./s |
|---|---|---|---|---|---|---|
| | | fication | 60° C. | None | 30 sec | 2.5 |
| | | | 72° C. | Single | 5 sec | 4.8 |
| Cooling | 1 | None | 40° C. | | 1 min | 2.5 |

Hepatotoxicity Assay

NHP-IPSC-derived hepatocytes were enriched using MACS and replated in matrigel sandwich condition as described above. To assess cell response to hepatotoxic compounds cells were treated with 100 µM troglitazone (Sigma) for 24 hours. Cell viability was measured using the WST-1 reagent (Sigma). 10 µl WST-1 reagent were added directly to the medium (1:10 dilution) and cells were incubated for 4 hours at 37° C., 5% $CO_2$. Plates were stirred for 15 seconds and absorbance at 405 nm was measured.

Example 1

Establishing a Protocol for the Generation of Hepatocytes from NHP-IPSCs

Culture Conditions for Feeder-Free Cultivation of NHP-IPSCs

To differentiate NHP-IPSCs into hepatocytes we tested a standard protocol to derive hepatocytes from human pluripotent stem cells. This protocol was developed for human pluripotent stem cells cultured in feeder-free conditions. (Cell Stem Cell. 2013 Feb. 7; 12(2):238-51. doi: 10.1016/j.stem.2012.11.011. Epub 2012 Dec. 13. A TALEN genome-editing system for generating human stem cell-based disease models. Ding Q1 & Cowan C A et al.). However, in these culture conditions, NHP-IPSCs did not commit towards the endoderm but differentiated to the neural lineage. Neural commitment of cynomolgus IPSCs was also already observed in standard culture conditions used for human pluripotent stem cells. Thus, culture conditions for differentiation as well as for pluripotent cells established for human IPSCs are not appropriate for NHP-IPSCs and differentiation protocols need to fulfill different criteria for NHP cells than for human cells. First, we developed feeder-free culture conditions for NHP-IPSCs by modifying a culture system established for monkey embryonic stem cells. Ono, T. et al. A single-cell and feeder-free culture system for monkey embryonic stem cells. PLoS One 9, e88346, doi:10.1371/journal.pone.0088346 (2014). In this study, a defined medium ("MT medium") was used in combination with collagen coating. We combined MT medium with MATRIGEL® coating as this combination proved most suitable to culture NHP-IPSCs in the pluripotent state as indicated by immunostaining for the pluripotency markers OCT4, SOX2, NANOG and negative staining for the neuroectodermal marker SOX1 (FIG. 1A-FIG. 1E). Thus, for the differentiation approaches described below, NHP-IPSCs cultured under these conditions were used.

Endoderm Induction in NHP-IPSCs

In vivo, hepatocytes arise from the endodermal lineage which differentiates into hepatic endoderm and further into hepatocytes. To derive hepatocytes from pluripotent stem cells, efficient endoderm induction is a crucial step. In human PSCs, endoderm formation can be induced by high concentrations of ActivinA in defined medium conditions. However, as these conditions did not show the expected effects in NHP-IPSC, we tested various combinations of growth factors, basic media and cell densities to induce endoderm commitment in monkey stem cells. Importantly, as monkey IPSCs seem to have a bias towards ectoderm commitment, we tested activation of Wnt signaling to inhibit ectoderm and enhance endoderm formation. Additionally, we analyzed the effect of MT basic medium on endoderm commitment as standard media used for human cells (e.g., RPMI) appeared to promote ectoderm formation in monkey cells.

Endoderm specification was analyzed by determining the number of cells positive for the endodermal markers FOXA2 and SOX17 on day 4 and day 7 of differentiation. Regarding the seeding cell number, the best results were obtained when using 45'000 cells/$cm^2$ with about 53% SOX17 and FOXA2 double positive cells for differentiation in RPMI medium as basic medium and 63% double positive cells for differentiation in MT medium as basic medium. This cell density was used in further experiments assessing the impact of different media compositions on endoderm formation (FIG. 2 depicts a schematic overview of these experiments). On day 4, we detected more FOXA2 and SOX17 positive cells in MT medium than in RPMI medium. Similar results were also observed on day 7, albeit the difference between the two media conditions was not as high on day 7 as that observed on day 4 (FIG. 3A and FIG. 3B). Thus, the combination of MT medium as basic medium and seeding number of 45000 cells/$cm^2$ was selected as optimal conditions to induce endoderm commitment in NHP IPSCs.

Next, we sought to assess the optimal conditions for hepatic endoderm specification as well as hepatocyte differentiation. Again, we focused on identifying the ideal media compositions for NHP-IPSCs, as previous experiments had shown that media established for human cells (e.g., HBM medium) were not suitable.

Thus, the differentiation was performed in either MT medium or RPMI medium and the maturation in either MT medium or HBM medium (FIG. 2).

Expression of α1AT and AFP at day 15 of differentiation as well as ALB at day 21 was used as marker for hepatocyte commitment and maturation, respectively. The comparison of the different media combinations showed the highest number of positive cells in the conditions MT/MT and RPMI/MT. Only few cells were stained in the conditions MT/HBM and RPMI/HBM indicating that HBM medium which is developed for human hepatocytes is not suitable for NHP cells (FIG. 4A).

This was also confirmed by analyzing the morphology of differentiated cells at day 28 of differentiation. Large areas of hepatocytes were present in MT/MT and RPMI/MT conditions which can be recognized by their morphology and the presence of lipid droplets. In MT/HBM and RPMI/HBM conditions almost no hepatocytes were generated, instead cells formed displayed fibroblast-like morphology or formed cyst-like structures (FIG. 4B).

Example 2

Optimization of Hepatocyte Differentiation

Having determined the ideal seeding number and the media combination MT/MT as best conditions for hepatocyte commitment, we sought to further optimize the protocol by testing various combinations of growth factors and small molecules in the protocol.

Thus, we tested the impact of prolonged addition of high ActivinA which has been shown to increase the amount of cells with endoderm commitment. Second, FGF10 treatment instead of FGF2 addition was tested as it has been reported that FGF10 can improve hepatocyte differentiation. Ogawa, et al., Development. 2013; 140: 3285-3296 Third, the Notch signaling is involved in bile duct formation (Jin, et al. Dongwuxue Yanjiu 2011; 32: 391-395; Wang, T. et al. Cell Tissue Res. 2014; 357: 173-184) and addition of DAPT to inhibit Notch signaling might prevent formation of cholangiocyte-like cells and therefore addition of DAPT from day 11 to day 20 was tested as well.

Cells were differentiated using combinations of all three modifications (FIG. 5). At day 21 of differentiation, efficiency of differentiation was analyzed using two different quantification methods. First, the area covered by ALB positive cells was determined and second the area of cells with typical hepatocyte morphology was evaluated (FIG. 6A and FIG. 6B).

The results show that FGF2 treatment resulted in more ALB positive cells than FGF10 treatment. Comparison of high and low ActivinA treatment in combination with FGF2 showed that there were more hepatocyte-like cells for prolonged high ActivinA treatment. DAPT treatment from day 11 to day 20 of differentiation did not induce a significant increase in differentiation efficiency. However, it was observed that cells were more homogenously distributed after addition of DAPT. Analysis of the ALB stained area showed that the Act100/FGF2/+DAPT condition had the lowest variance between the three replicates. Therefore, this combination was determined as most efficient approach for hepatocyte differentiation leading to about 20% SCARB1 positive cells.

Example 3

Characterization of NHP-IPSC Derived Hepatocytes

As previously shown in Example 1, NHP-IPSC-derived hepatocytes displayed hepatocyte morphology and expressed characteristic markers such as AFP, ALB, and α1AT. To further characterize the cells, we analyzed their capacity of typical hepatic functions (FIG. 7A-FIG. 7E). Bodipy staining showed the presence of numerous intracellular lipid vesicles in cells with hepatocyte morphology indicating their ability of lipid storage. Similarly, glycogen storage could be visualized by PAS staining. These results suggest that NHP-IPSC derived cells had adopted typical hepatic storage functions. Moreover, cells were capable of uptake and release of indocyanin green, a process requiring the presence of specific transporter proteins characteristic for hepatocytes.

Last, we analyzed the expression of CYP450 enzymes as these proteins are responsible for numerous metabolic activities of hepatocytes. We treated the cells with Rifampicin and Dexamethasone which are both known to induce expression of CYP enzymes. Quantitative real time PCR revealed that CYP mRNAs were upregulated in differentiated cells compared to undifferentiated NHP-IPSCs albeit expression levels were lower than in primary hepatocytes (FIG. 8A). This might be due to the fact that IPSC-derived cells are less mature than the corresponding primary cells. Alternatively, the heterogeneous composition of the stem cell-derived cultures might result in a reduced signal for CYP mRNAs as non-hepatocytes present in the culture might dilute the signal.

Treatment with Rifampicin resulted in an increase in CYP mRNA expression in both primary and IPSC-derived hepatocytes while Dexamethasone induced CYP expression only in primary cells (FIG. 8B, FIG. 8C). Results of CYP activity analysis were in line with mRNA expression: In IPSC-derived cells CYP activity was increased upon Rifampicin treatment while Dexamethasone did not induce CYP activity (FIG. 8D).

In summary, these findings show that NHP-IPSC-derived cells display key feature of hepatocytes, such as lipid and glycogen storage, transporter activity and expression of CYP enzymes.

Example 4

Replating and Sorting Strategies

Stem cell-derived somatic cell types have a great potential as in vitro system for drug screening, especially if the corresponding primary cell type is not available or only in limited quantities as it is the case for hepatocytes. However, drug screening requires the availability of cells in suitable plate formats. For this purpose, we tested different strategies to replate hepatocytes derived from NHP-IPSCs. As mature hepatocytes are sensitive cells growing in dense clusters, replating approaches should enable efficient detachment of cells while not affecting their viability. After testing of various dissociation reagents, most conditions did not result in subsequent cell attachment or attachment of other cells but not hepatocytes. Only dissociation with Accutase for 3 hours and dissociation with 0.05% trypsin for 3 hours led to attachment of hepatocytes which expressed Albumin (FIG. 9A). Further optimization identified Accutase treatment of 1 hour as suitable for efficient detachment while not negatively influencing cell viability (FIG. 9B).

Another requirement for efficient application of cell models in drug screening is the generation of a pure culture of the desired cell type. For this purpose, we sought to identify hepatocyte-specific surface proteins that could be used for cell sorting strategies. For human cells, it has been shown that ASGR1 can be used as surface marker to enrich for hepatocytes (Basma, H. et al. Gastroenterology. 2009; 136: 990-999). However, no ASGR1 positive cells could be detected in NHP cells at day 22 and day 28 of differentiation making it necessary to identify other suitable surface antigens (FIG. 10). Analysis of several potential candidates revealed SCARB1 as potential marker for cell sorting as SCARB1 expression was found in NHP cells subjected to hepatocyte differentiation protocol, but was absent in NHP IPSCs. SCARB1 is, along with CD81, the receptor for the entry of the Hepatitis C virus in liver cells and therefore is indicative for mature hepatocytes.

Thus, we performed magnetic associated cell sorting of NHP-IPSC derived cells. Flow cytometry analysis revealed that this strategy led to an enrichment of SCARB1 positive cells from 20% up to 80% (FIG. 11A). 24 hours after replating, the majority of cells in the SCARB1 positive fraction showed typical hepatocyte morphology (FIG. 11C). Gene expression analysis of sorted and unsorted cells revealed higher expression levels of hepatocyte-specific genes in SCARB1 positive cells further confirming that the sorting procedure resulted in an enrichment of hepatocytes (FIG. 11B).

Next, we sought to identify conditions allowing culture of IPSC-hepatocytes after replating for at least 5 to 7 days to ensure feasibility of this cell system for various assays. We tested different coating strategies known to be suitable for hepatic cell types, namely Laminin, Collagen and MATRIGEL® sandwich culture (see material and methods for details). Cells attached on all matrices tested, however, in MATRIGEL® sandwich culture, cell morphology was better compared to other matrices (FIG. 11C). Thus, MATRIGEL® sandwich coating was defined as best condition for culture of NHP-IPSC-hepatocytes.

Example 5

Application of NHP-IPSC Derived Hepatocytes as In Vitro System

Stem cell-derived hepatocytes represent a promising in vitro system for basic and translational research as well as for drug development. Important applications are analysis of drug-induced liver injury or the as model systems for infections with liver-specific pathogens. Currently, primary hepatocytes are used for this purposes, however, they are linked to various disadvantages like their limited availability and the variability between different donors/batches. Several studies report successful implementation of human stem cell-derived hepatocytes as in vitro systems, however, for NHPs primary cells are currently the only option.

To assess the feasibility of NHP IPSC-derived hepatocytes as model system for drug-induced liver injury, we treated the hepatocytes with Troglitazone, a small molecule with known hepatotoxic effects. After 24 hours, a decrease in cell viability was detected in Troglitazone-treated NHP IPSC-derived hepatocytes compared to control cells (FIG. 12). These data suggest that NHP IPSC-derived hepatocytes can be used as in vitro system to evaluate hepatotoxicity.

Next, we sought to evaluate the feasibility of NHP IPSC-derived hepatocytes as in vitro system for liver injury induced by oligonucleotides developed for antisense therapy. Oligonucleotide therapy can cause severe hepatocyte toxicity because the oligonucleotides accumulate in the liver. There is a need for relevant in vitro systems to model these effects to evaluate oligonucleotide candidates prior to in vivo studies. Thus, NHP IPSC-derived hepatocytes were treated with oligonucleotides which are known to be toxic in mice. In vivo toxicity could be reproduced in NHP IPSC-derived hepatocytes suggesting these cells as relevant model to evaluate oligonucleotide safety in NHPs. Importantly, these effects could not be modeled in NHP primary hepatocytes potentially due to the fact that these cells dedifferentiate rapidly in culture. This underlines the advantages of the IPSC-based hepatocyte system as it allows unlimited supply of cells responsive to oligonucleotide toxicity in vitro.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method for differentiating non-human primate (NHP) pluripotent stem cells into NHP hepatocytes, the method comprising:
    a) providing NHP pluripotent stem cells in a feeder-free culture in a chemically defined medium;
    b) contacting the NHP pluripotent stem cells with a Wnt signaling activator to produce endodermal cells;
    c) contacting the endodermal cells with bone morphogenetic protein 4 (BMP4) and a fibroblast growth factor to produce immature NHP hepatocytes; and
    d) contacting the immature NHP hepatocytes with hepatocyte growth factor (HGF), OncostatinM and Dexamethasone to produce NHP hepatocytes,
    wherein the NHP pluripotent stem cells are from Cynomolgus monkey (*Macaca fascicularis*).

2. The method of claim 1, wherein the Wnt signaling activator is (3-(3-Amino-phenyl)-4-(1-methyl-1H-indol-3-yl)-pyrrole-2,5-dione.

3. The method of claim 1, wherein step b) comprises contacting the cells with Ly294002 and (3-(3-Amino-phenyl)-4-(1-methyl-1H-indol-3-yl)-pyrrole-2,5-dione to induce differentiation.

4. The method of claim 1, wherein step b) further comprises contacting the cells with LDN193189.

5. The method of claim 1, wherein step b) comprises contacting the cells with knock-out serum replacement (KSR) and DMSO.

6. The method of claim 1, wherein the fibroblast growth factor is FGF2 or FGF10.

7. The method of claim 6, wherein step c) further comprises contacting the cells with DMSO.

8. The method of claim 1, wherein step d) further comprises contacting the cells with a NOTCH signaling inhibitor.

9. The method of claim 1, wherein the NHP pluripotent stem cells of step a) are induced pluripotent stem cells (iPSCs).

10. A NHP hepatocyte obtained by the method according to claim 1.

11. A biobank of NHP hepatocytes obtained by the method according to claim 1.

* * * * *